(12) United States Patent
Needleman et al.

(10) Patent No.: US 8,591,533 B2
(45) Date of Patent: Nov. 26, 2013

(54) ENDOLUMENAL RESTRICTION METHOD AND APPARATUS

(75) Inventors: Bradley J. Needleman, Columbus, OH (US); Jeffrey W. Hazey, Dublin, OH (US); Richard Peters, Gahanna, OH (US)

(73) Assignee: The Ohio State University Research Foundation, Columbus, OH (US)

(*) Notice: Subject to any disclaimer, the term of this patent is extended or adjusted under 35 U.S.C. 154(b) by 753 days.

(21) Appl. No.: 12/526,157

(22) PCT Filed: Feb. 6, 2008

(86) PCT No.: PCT/US2008/001586
§ 371 (c)(1), (2), (4) Date: Sep. 17, 2009

(87) PCT Pub. No.: WO2008/097586
PCT Pub. Date: Aug. 14, 2008

(65) Prior Publication Data
US 2010/0324572 A1    Dec. 23, 2010

Related U.S. Application Data

(60) Provisional application No. 60/899,713, filed on Feb. 6, 2007, provisional application No. 60/967,666, filed on Sep. 6, 2007.

(51) Int. Cl.
A61B 17/08    (2006.01)

(52) U.S. Cl.
USPC .......................................... 606/151

(58) Field of Classification Search
USPC ............ 606/139, 142, 151, 153, 219; 600/37
See application file for complete search history.

(56) References Cited

U.S. PATENT DOCUMENTS

| | | | |
|---|---|---|---|
| 4,592,339 A | 6/1986 | Kuzmak et al. | |
| 4,595,007 A * | 6/1986 | Mericle | 606/221 |
| 4,804,791 A | 2/1989 | Kitson et al. | |
| 5,088,979 A * | 2/1992 | Filipi et al. | 604/26 |
| 5,188,636 A | 2/1993 | Fedotov | |
| 5,545,179 A | 8/1996 | Williamson, IV | |
| 5,810,851 A | 9/1998 | Yoon | |
| 5,964,772 A | 10/1999 | Bolduc et al. | |

(Continued)

FOREIGN PATENT DOCUMENTS

| | | |
|---|---|---|
| WO | WO0215796 A2 | 2/2002 |
| WO | WO2005079673 A2 | 9/2005 |
| WO | WO2005092210 A1 | 10/2005 |
| WO | WO2008097586 A2 | 8/2008 |

OTHER PUBLICATIONS

The Cleveland Clinic Foundation, Surgical Options for Severe Obesity, The Cleveland Clinic Health Information Center Website, Dec. 21, 2006.

(Continued)

*Primary Examiner* — Darwin Erezo
(74) *Attorney, Agent, or Firm* — Meunier Carlin & Curfman, LLC

(57) ABSTRACT

An apparatus and method for non-surgically creating a restriction in a tissue is provided where a binding mechanism (36) is inserted into the issue. This invention also relates to an apparatus for creating a stoma of variable and reproducible size in a hollow organ.

23 Claims, 27 Drawing Sheets

(56) References Cited

U.S. PATENT DOCUMENTS

| | | | |
|---|---|---|---|
| 6,140,545 A | 10/2000 | Merger et al. | |
| 6,149,667 A | 11/2000 | Hovland et al. | |
| 6,558,400 B2 * | 5/2003 | Deem et al. | 606/151 |
| 6,558,429 B2 | 5/2003 | Taylor | |
| 6,675,809 B2 | 1/2004 | Stack et al. | |
| 6,726,677 B1 | 4/2004 | Flaherty et al. | |
| 6,740,098 B2 | 5/2004 | Abrams et al. | |
| 6,773,440 B2 * | 8/2004 | Gannoe et al. | 606/142 |
| 6,790,214 B2 * | 9/2004 | Kraemer et al. | 606/153 |
| 6,884,248 B2 * | 4/2005 | Bolduc et al. | 606/143 |
| 6,927,048 B2 | 8/2005 | Verser et al. | |
| 7,077,850 B2 | 7/2006 | Kortenbach | |
| 7,083,629 B2 | 8/2006 | Weller et al. | |
| 7,121,283 B2 | 10/2006 | Stack et al. | |
| 7,141,055 B2 * | 11/2006 | Abrams et al. | 606/115 |
| 7,354,454 B2 | 4/2008 | Stack et al. | |
| 7,510,559 B2 * | 3/2009 | Deem et al. | 606/151 |
| 7,615,064 B2 * | 11/2009 | Bjerken | 606/153 |
| 7,618,426 B2 | 11/2009 | Ewers et al. | |
| 7,674,271 B2 * | 3/2010 | Bjerken | 606/144 |
| 7,704,264 B2 | 4/2010 | Ewers et al. | |
| 7,942,887 B2 * | 5/2011 | Kraemer et al. | 606/151 |
| 7,955,340 B2 * | 6/2011 | Michlitsch et al. | 606/139 |
| 8,137,366 B2 * | 3/2012 | Deem et al. | 606/151 |
| 2003/0055313 A1 | 3/2003 | Anderson et al. | |
| 2004/0006351 A1 | 1/2004 | Gannoe et al. | |
| 2004/0082963 A1 | 4/2004 | Gannoe et al. | |
| 2004/0092892 A1 | 5/2004 | Kagan et al. | |
| 2004/0133219 A1 | 7/2004 | Forsell | |
| 2005/0070931 A1 | 3/2005 | Li et al. | |
| 2005/0075654 A1 | 4/2005 | Kelleher | |
| 2005/0080444 A1 * | 4/2005 | Kraemer et al. | 606/192 |
| 2005/0192599 A1 | 9/2005 | Demarais | |
| 2005/0192601 A1 | 9/2005 | Demarais | |
| 2006/0199981 A1 | 9/2006 | Schuchardt et al. | |
| 2006/0253130 A1 | 11/2006 | Wolniewicz, III | |
| 2006/0253142 A1 | 11/2006 | Bjerken | |
| 2006/0264983 A1 | 11/2006 | Holsten et al. | |
| 2006/0264984 A1 | 11/2006 | Schurr et al. | |
| 2007/0005082 A1 * | 1/2007 | Kraemer et al. | 606/153 |
| 2007/0032807 A1 | 2/2007 | Ortiz et al. | |
| 2007/0073318 A1 | 3/2007 | Carter et al. | |
| 2007/0073323 A1 | 3/2007 | Carter et al. | |
| 2007/0112363 A1 | 5/2007 | Adams | |
| 2008/0172074 A1 | 7/2008 | Baker et al. | |
| 2009/0177214 A1 | 7/2009 | Adams | |
| 2009/0255544 A1 | 10/2009 | Cox | |
| 2009/0318936 A1 | 12/2009 | Harris et al. | |
| 2010/0010457 A1 | 1/2010 | Ewers et al. | |

OTHER PUBLICATIONS

Bard Endocinch website excerpts, www.endocinch.com/doc_bard.cfm, Jan. 1, 2001.

PCT/US2008/001586 Search Report, issued Aug. 11, 2009.

* cited by examiner

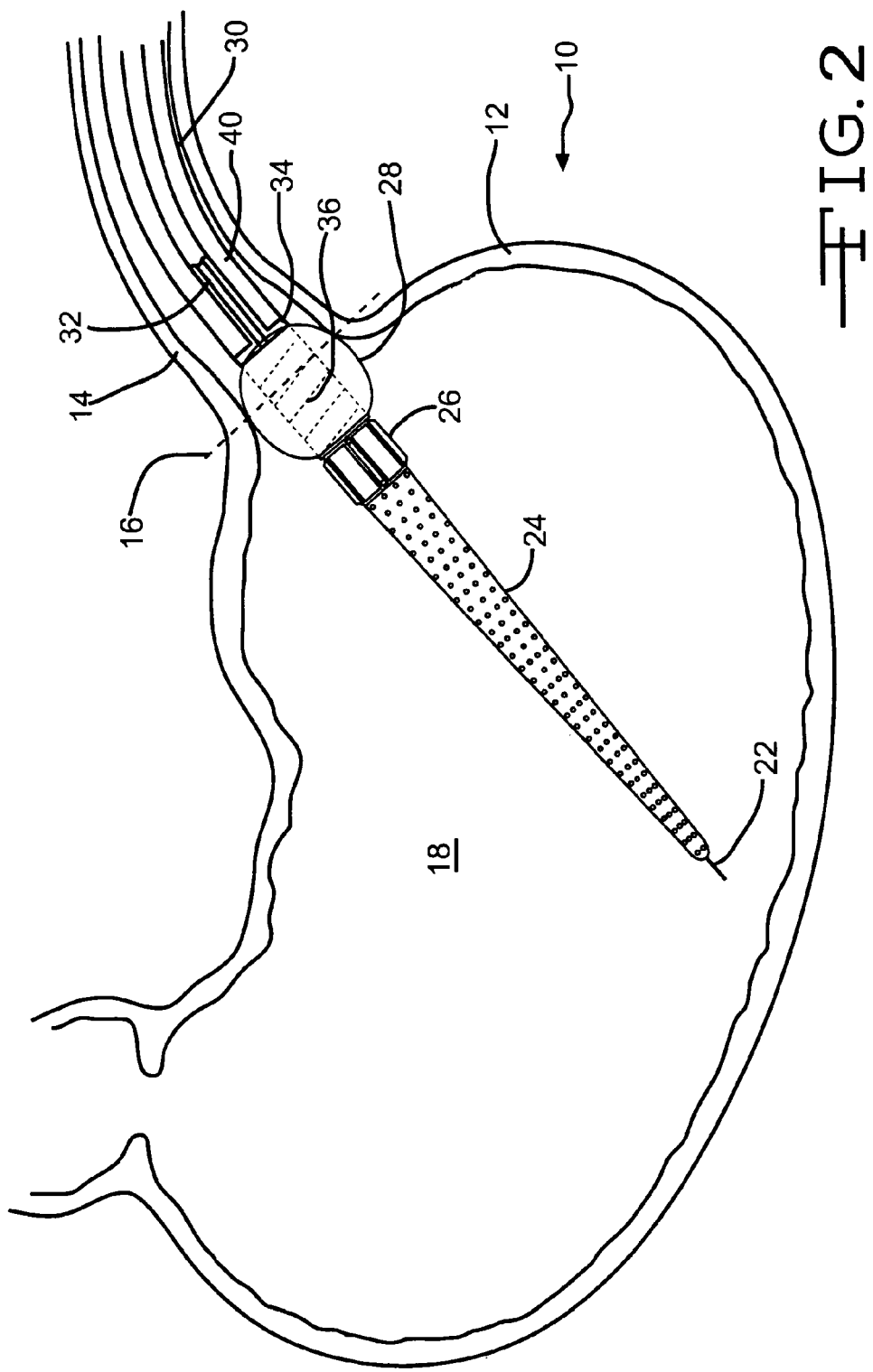

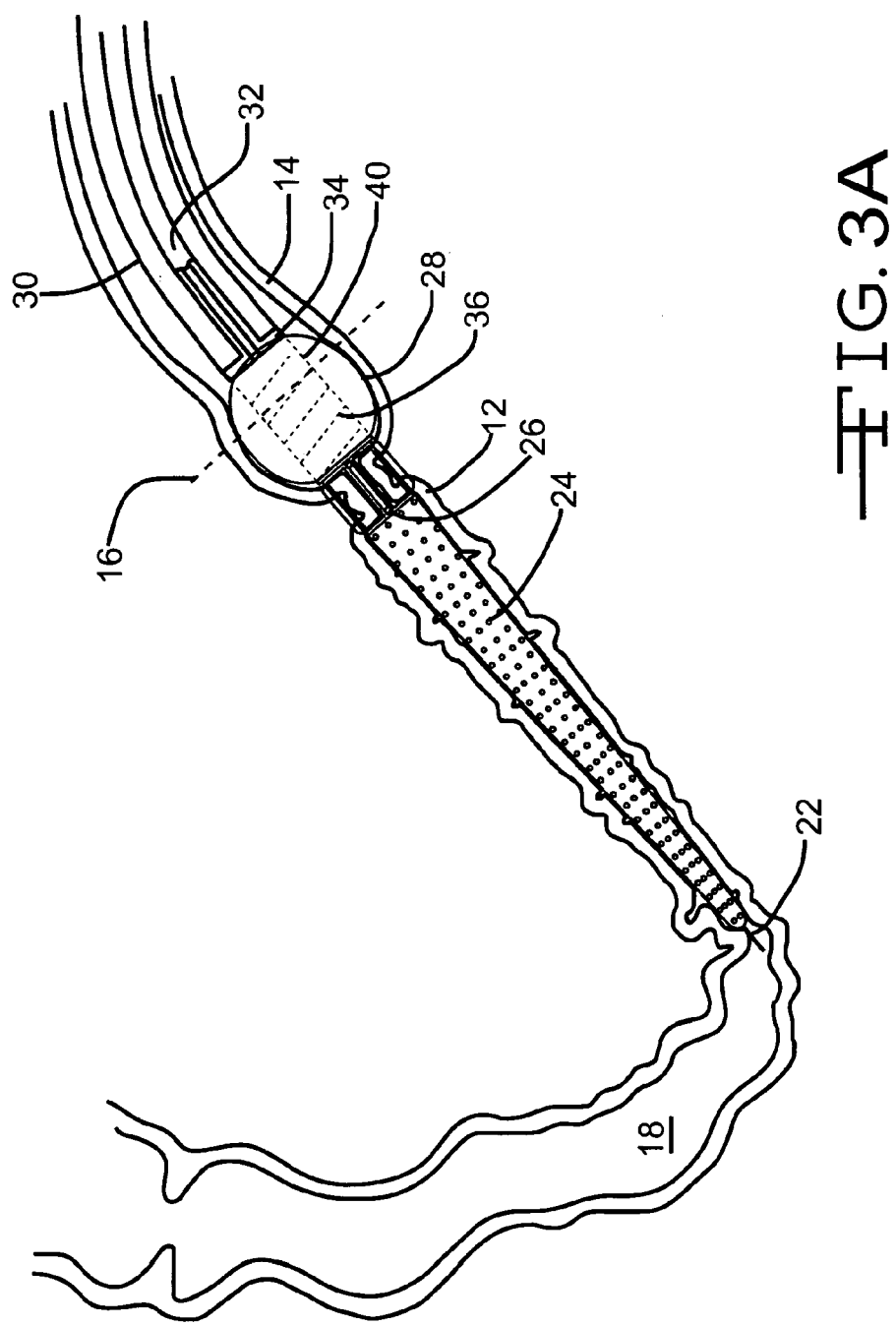

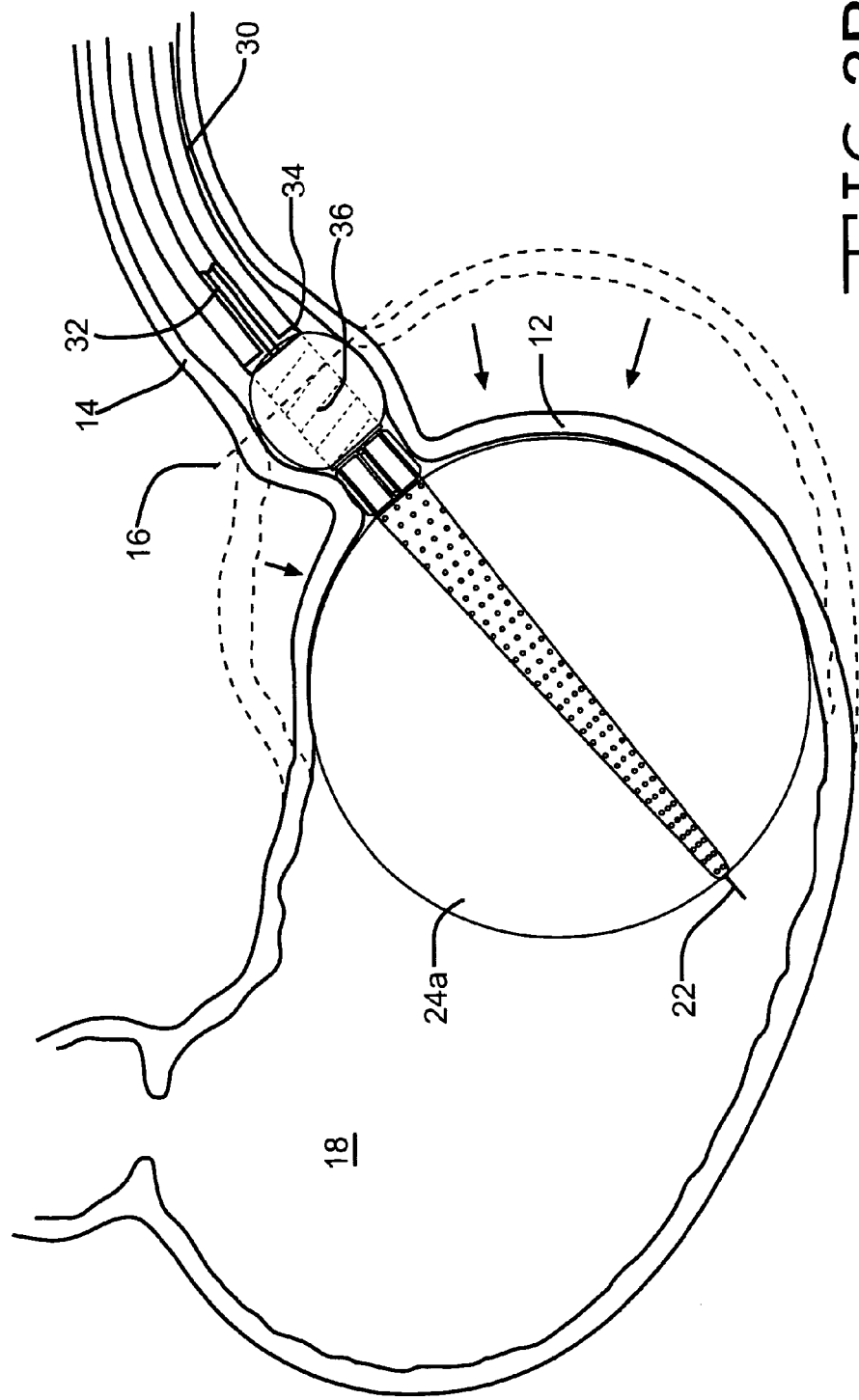

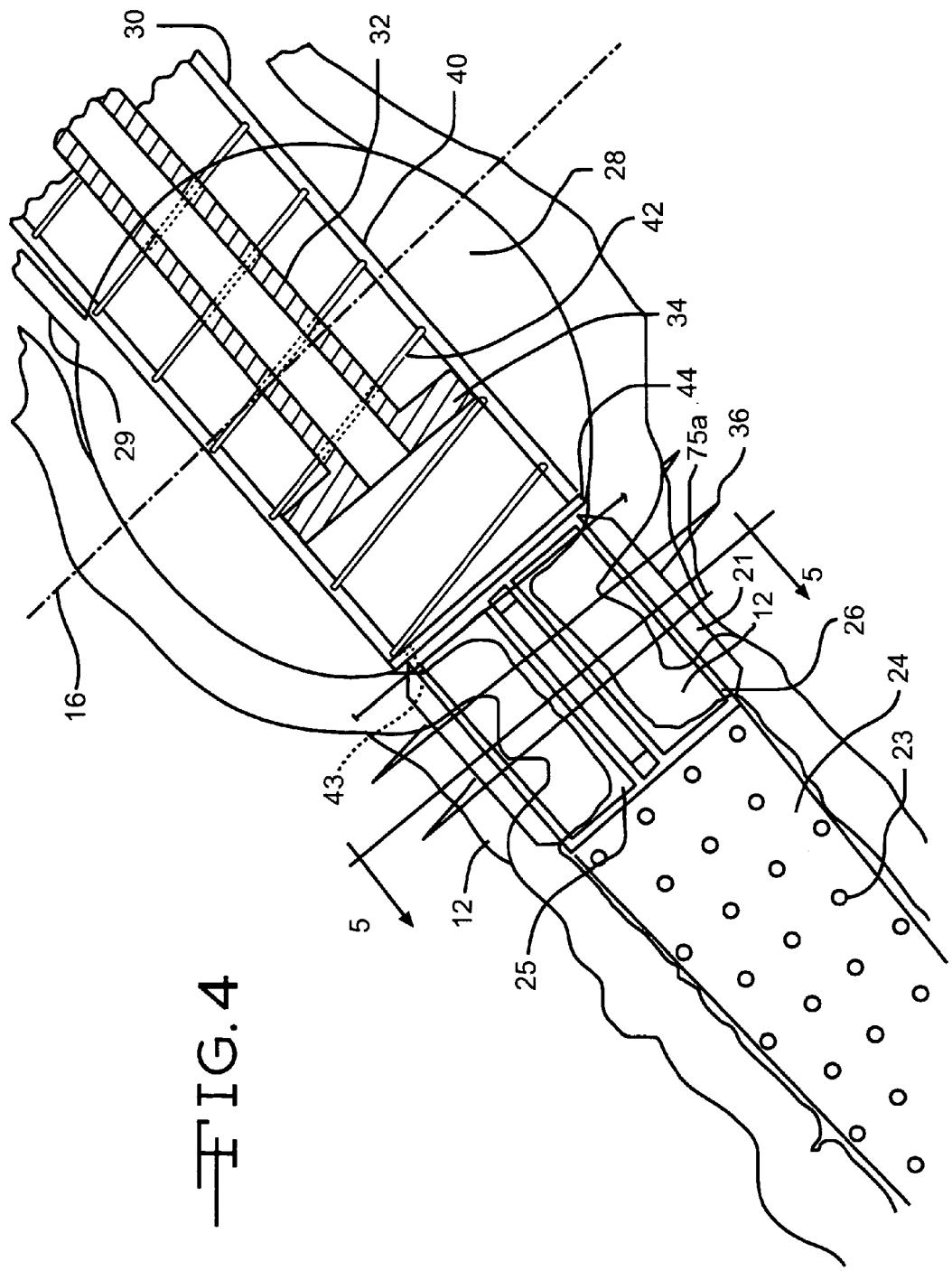

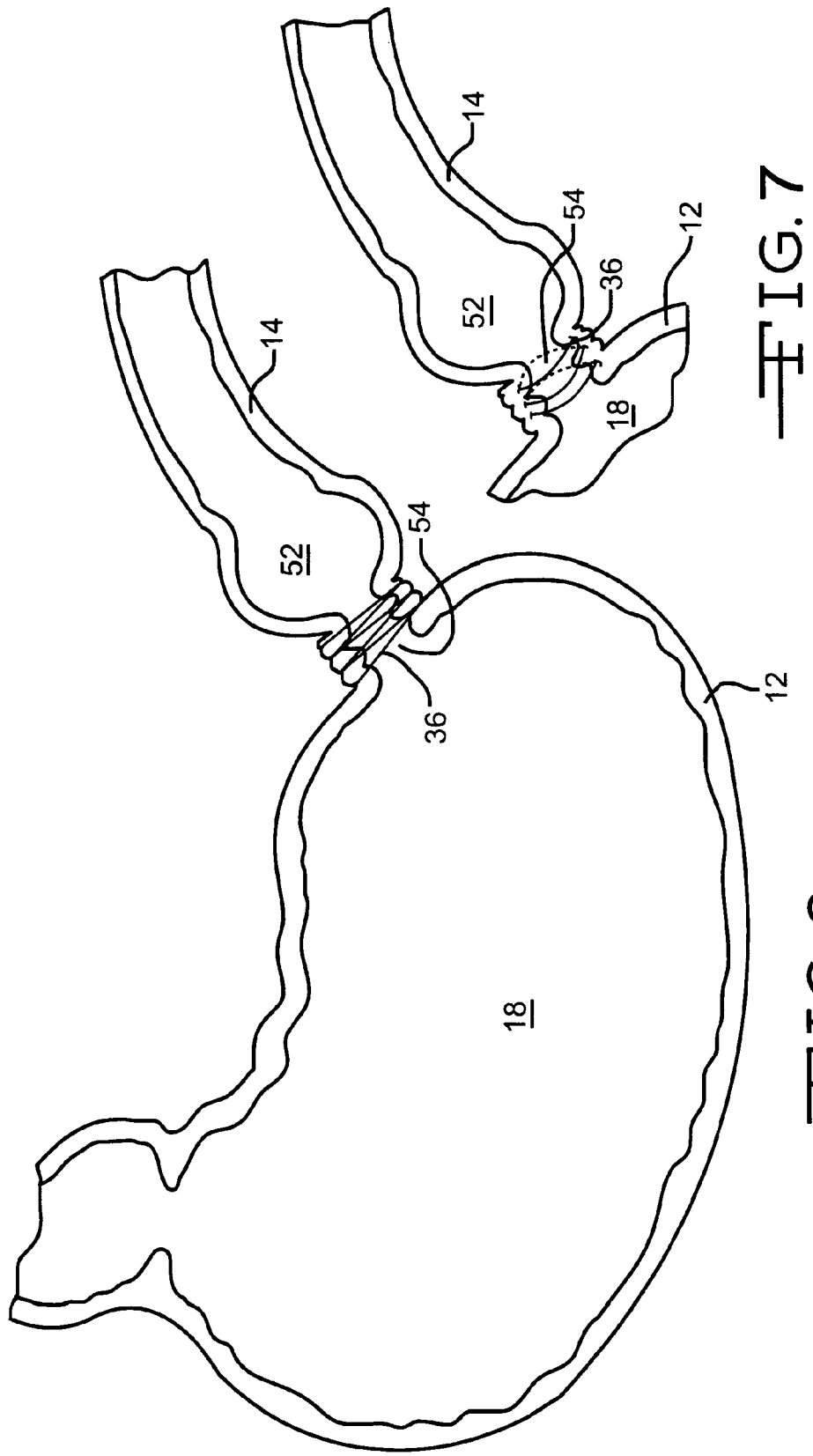

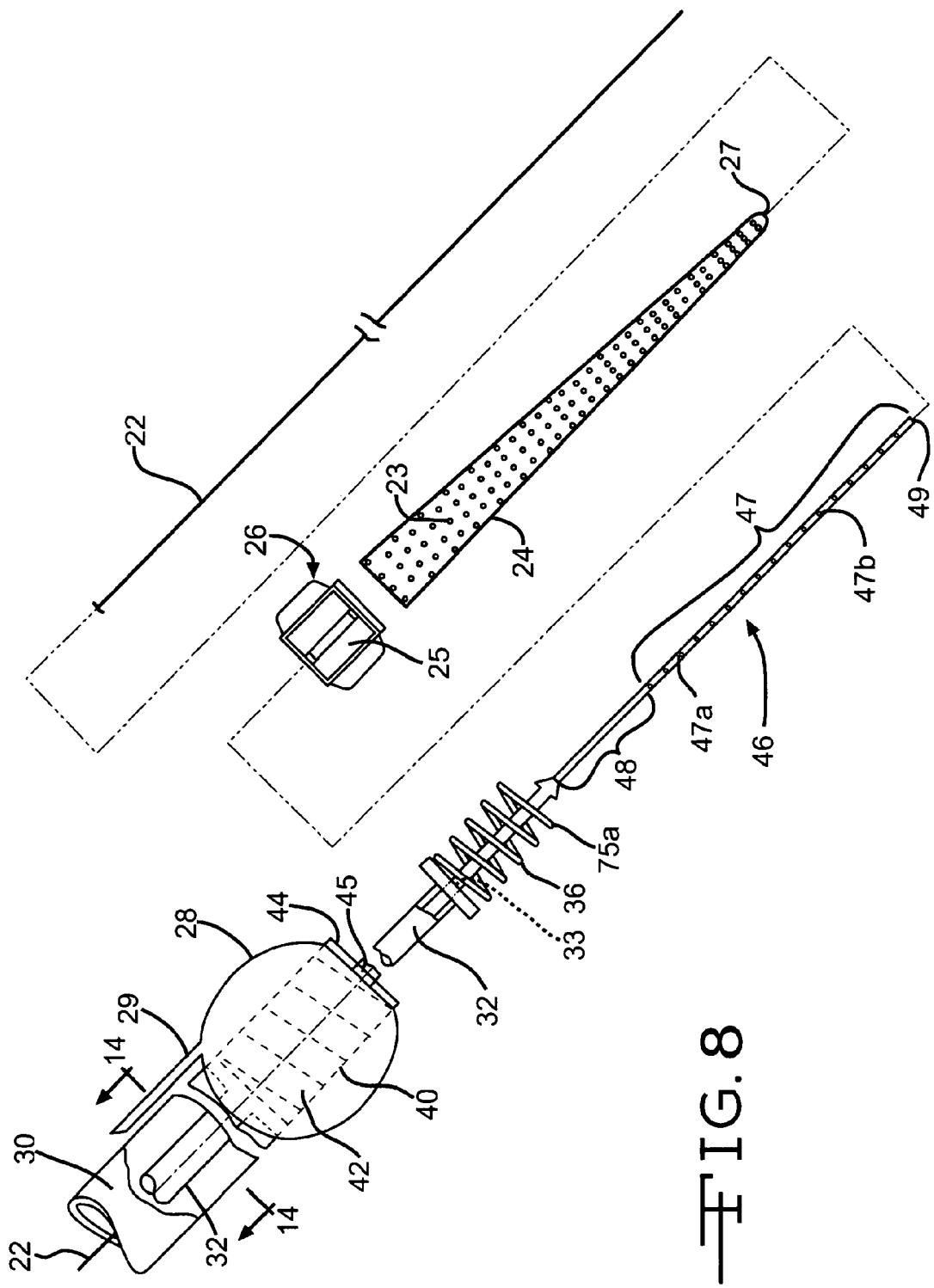

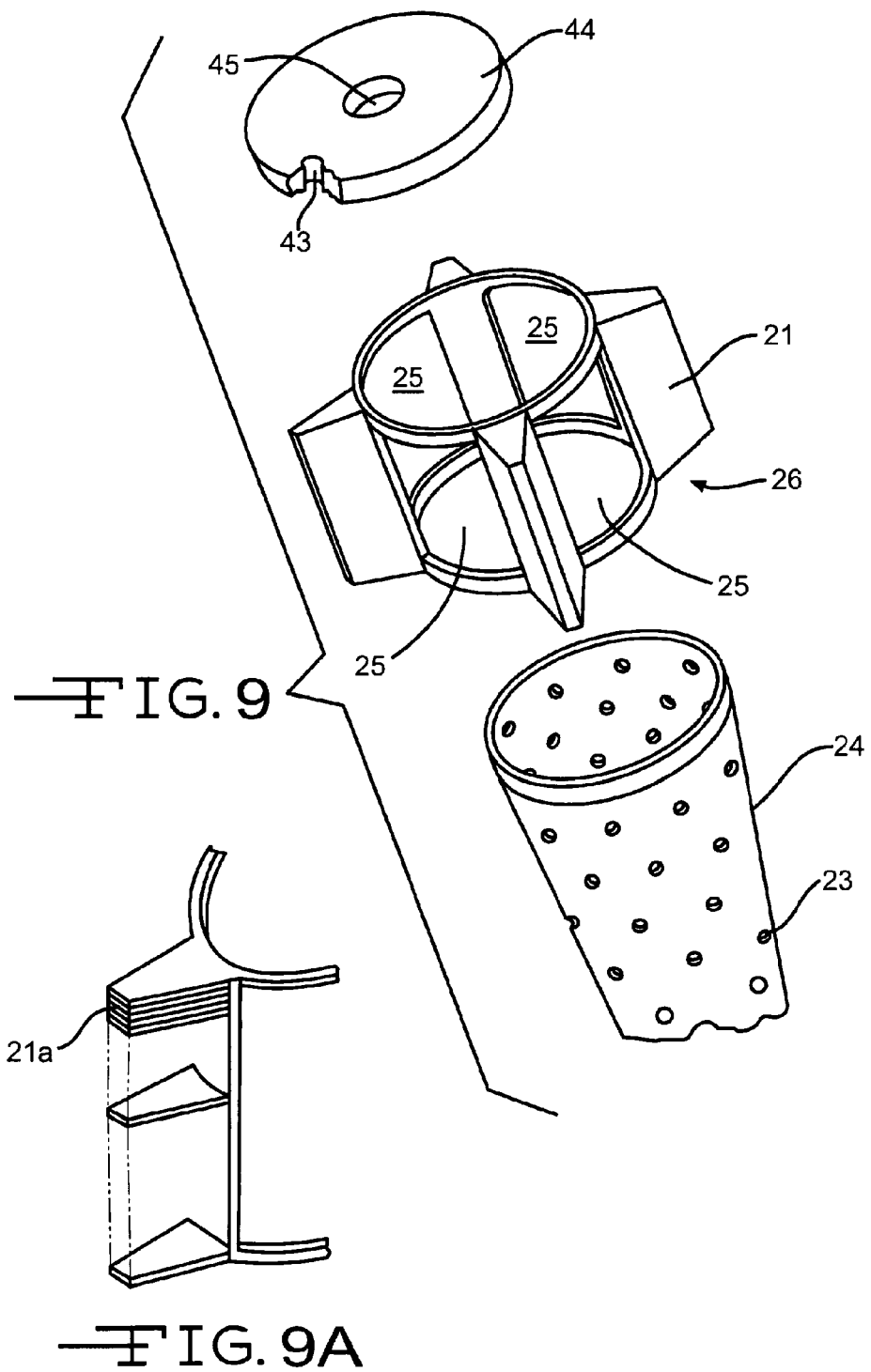

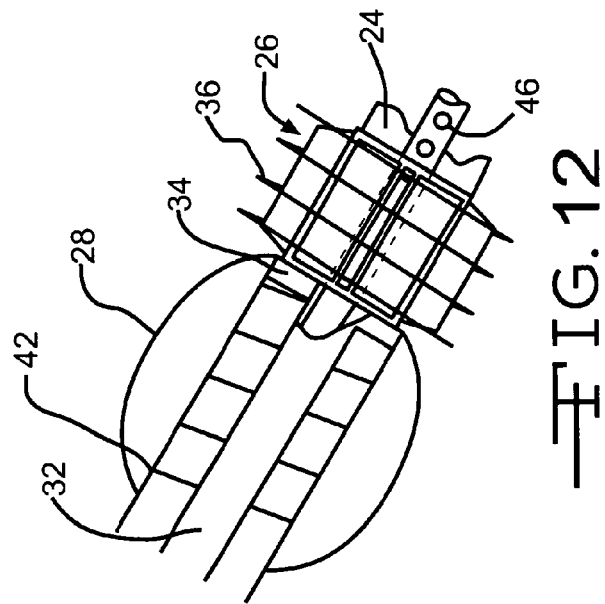
FIG. 12
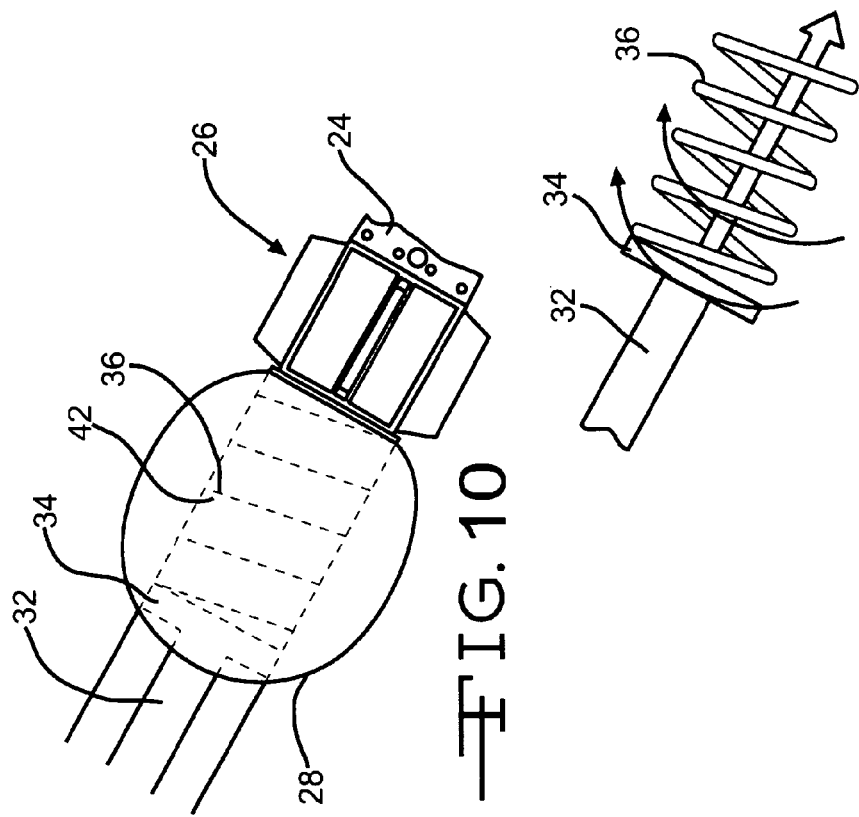
FIG. 11
FIG. 10

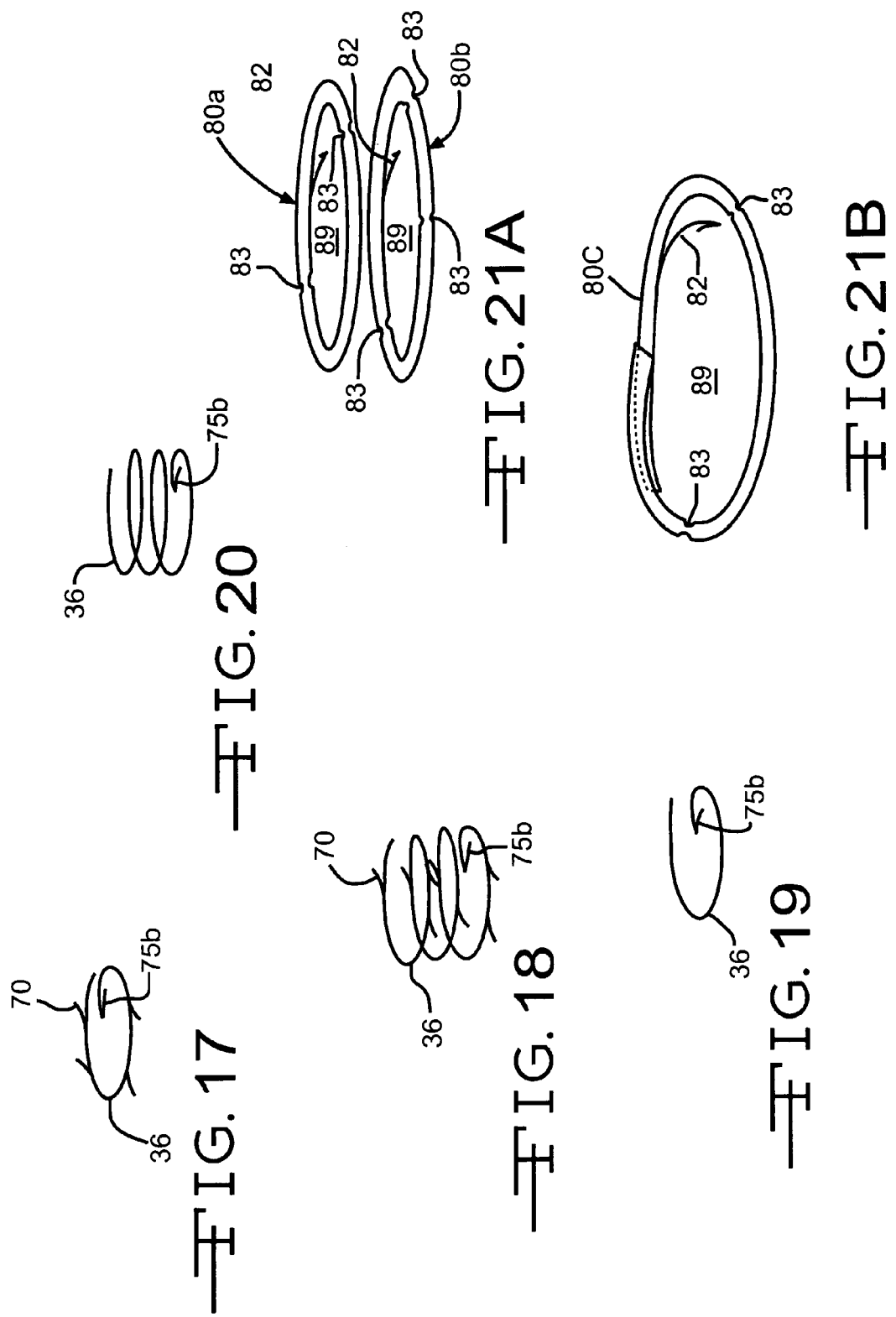

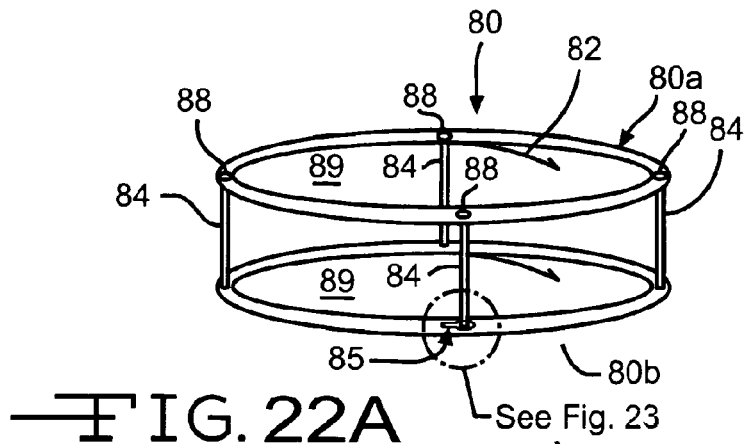
FIG. 22A
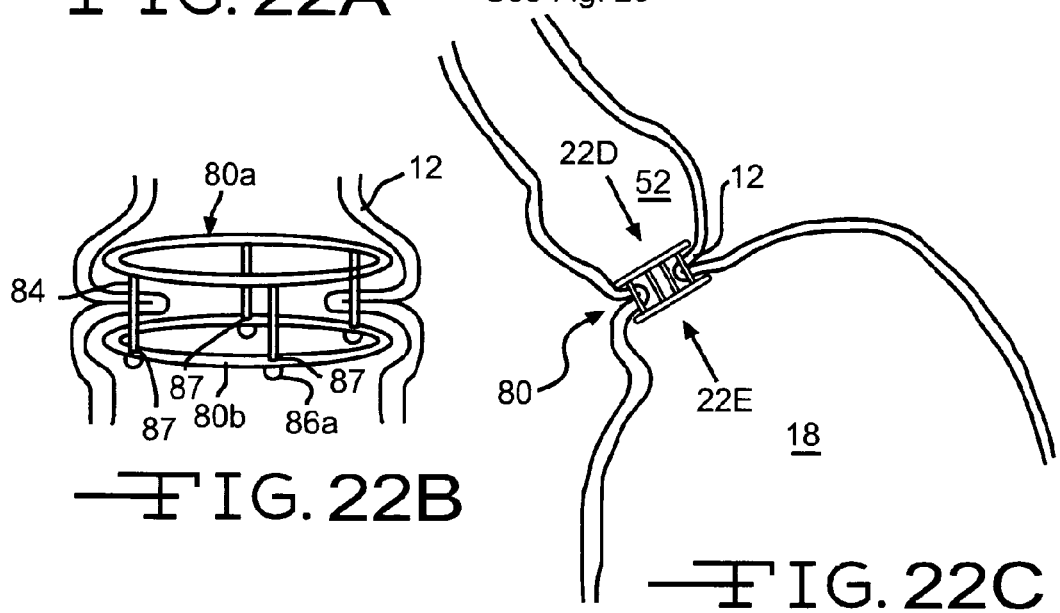
FIG. 22B
FIG. 22C
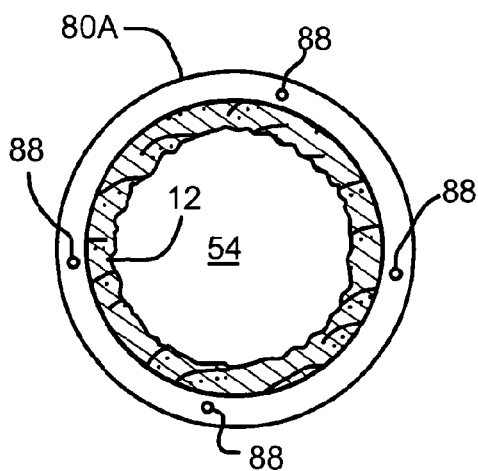
FIG. 22D
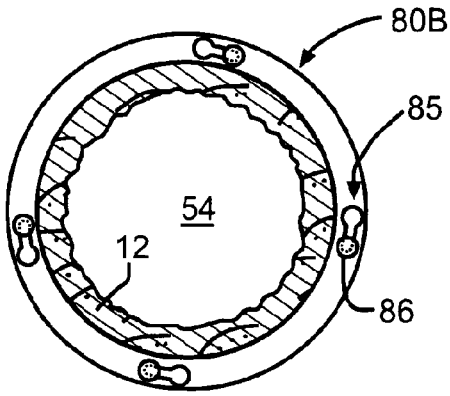
FIG. 22E

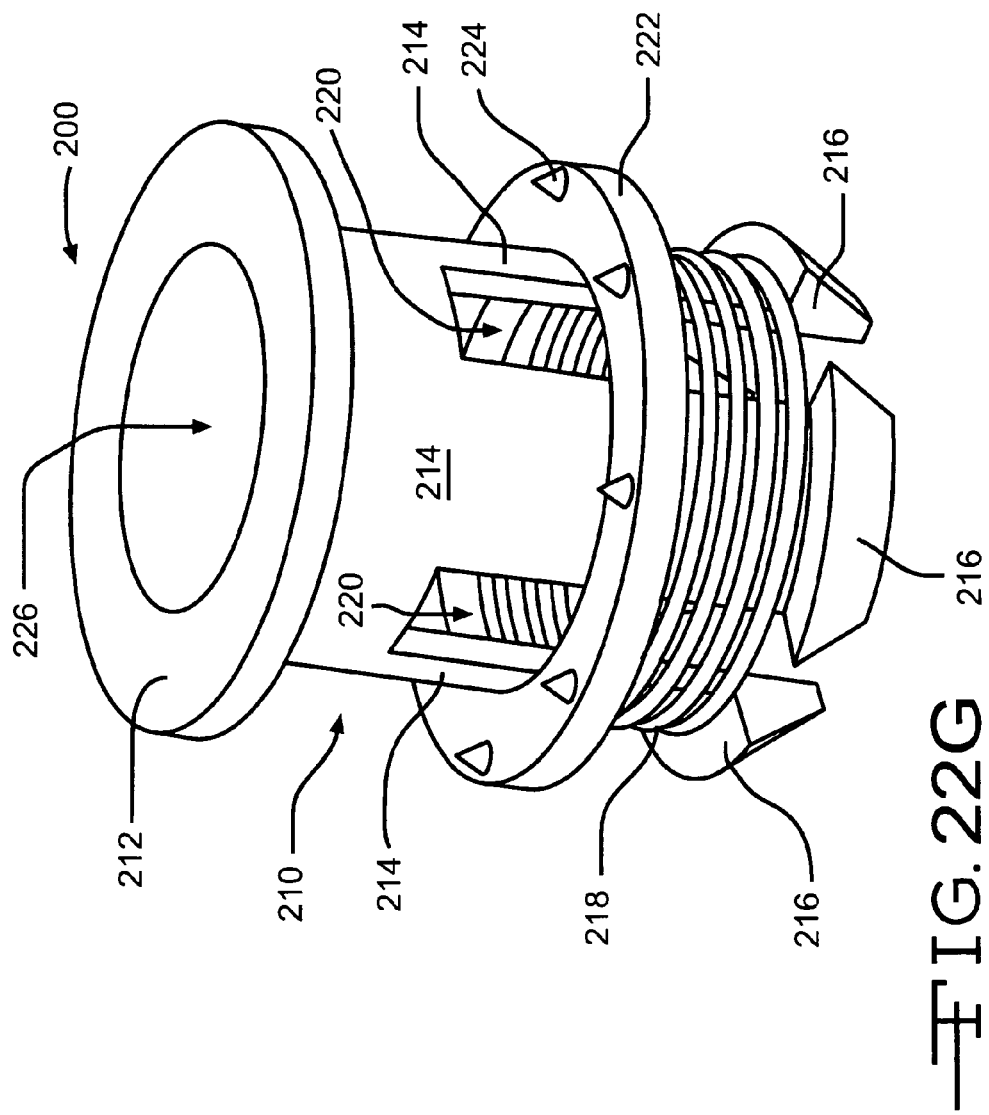

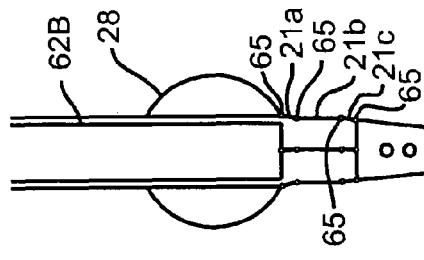
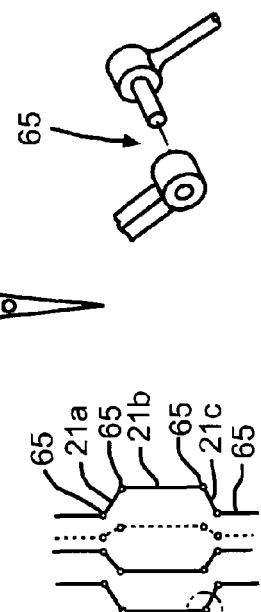
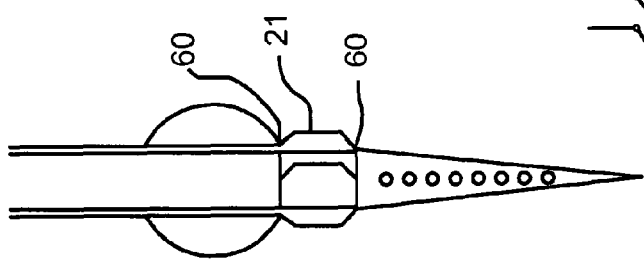
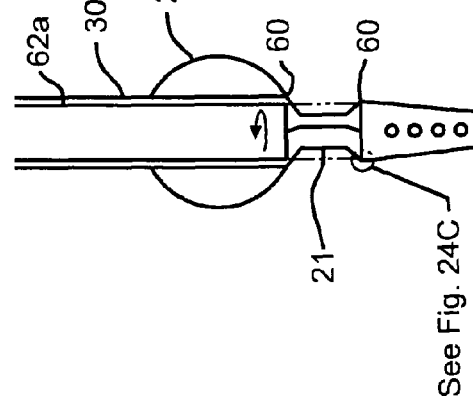
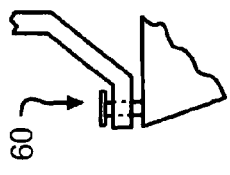

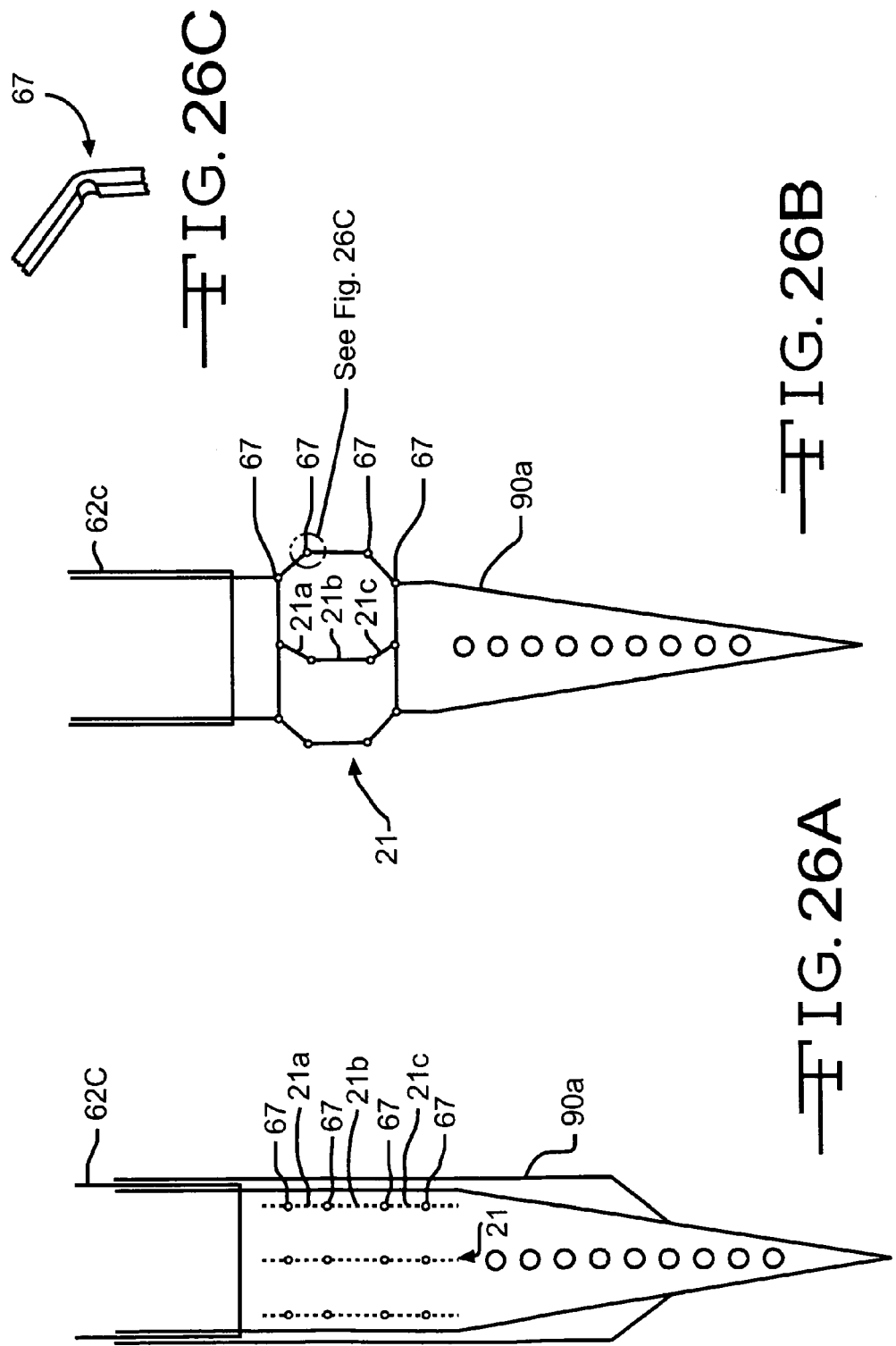

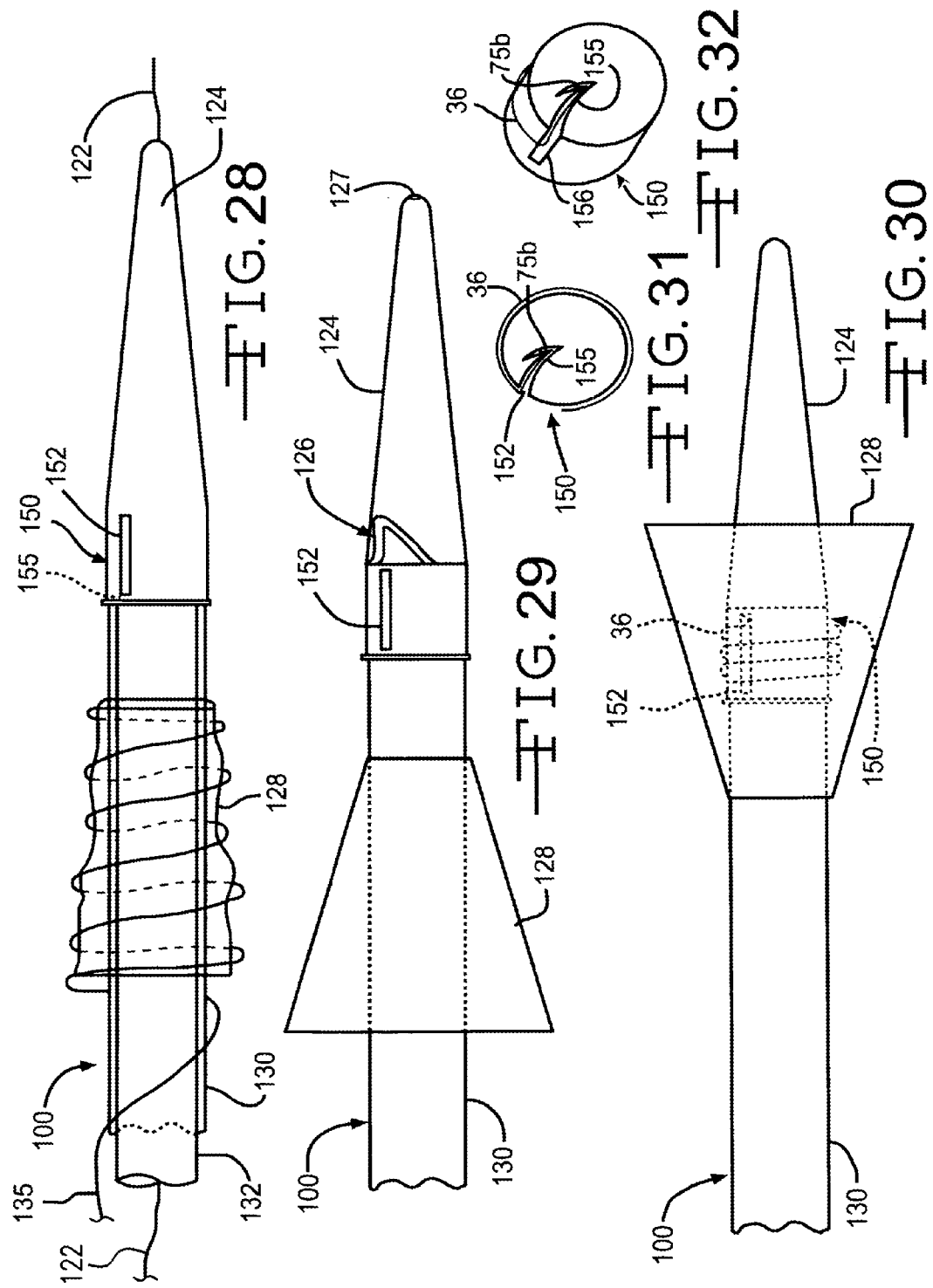

ENDOLUMENAL RESTRICTION METHOD AND APPARATUS

CROSS-REFERENCE TO RELATED APPLICATIONS

This application claims the benefit of U.S. Provisional Application No. 60/899,713, filed Feb. 6, 2007, and U.S. Provisional Application No. 60/967,666, filed Sep. 6, 2007, the disclosures of which are expressly incorporated herein by reference.

STATEMENT REGARDING FEDERALLY SPONSORED RESEARCH

This invention was not made with any Government support and the Government has no rights in this invention. The present invention claims the benefit of the PCT/US2008/001586 filed Feb. 6, 2008, which claims priority to U.S. Provisional Application No. 60/899,713, filed Feb. 6, 2007, and U.S. Provisional Application No. 60/967,666, filed Sep. 6, 2007.

TECHNICAL FIELD AND INDUSTRIAL APPLICABILITY OF THE INVENTION

This invention relates in general to a method and apparatus for creating a constriction in an opening. In particular, this invention relates to a method and apparatus for creating a stoma of a variable and reproducible size in a hollow organ.

BACKGROUND OF THE INVENTION

The prevalence of obesity has steadily increased over the years among both genders, all ages, all racial/ethnic groups, all educational levels, and all smoking levels. However, the number of people who are overweight and those exhibiting obesity generally increases with advancing age, then starts to decline among people over 60.

Medical treatment for obesity is met with discouraging results. Approximately 95% of people who begin weight loss programs will regain their weight within two years of their maximal weight loss. In the United States today there are approximately 170,000 primary operations performed for weight loss each year. 86% of operations are restrictive including the Roux-en-Y Gastric Bypass (70%) and the Lap Band procedure (16%). The remainders of operations performed in the United States are malabsorptive procedures such as the biliopancreatic diversion and duodenal switch (12%).

The conventional Roux-en-Y Gastric Bypass is considered the "gold-standard" operation. The components of a successful operation include a small gastric pouch of approximately 30 cubic centimeters (cc), (or the size of an egg), a small pouch outlet of approximately 12 millimeters (mm), (or the size of a dime), connecting to a Roux limb (or small bowel limb) that can be 60 to 200 centimeters (cm) in length. This operation imparts a feeling of early satiety upon the patients causing them to eat significantly less food at one time. Patients must chew their food well, eat slowly and stop when full otherwise they will encounter pain, nausea, and vomiting. In addition to early satiety, foods high in sugar content are restricted due to the potential for a dumping syndrome. Weight loss is immediate with this procedure with maximal weight loss seen in 18-24 months after surgery. Excess body weight loss is estimated to be between 60-80% during this time with improvement or resolution of many weight-related comorbidities.

The Roux-en-Y gastric bypass is traditionally performed through open surgery or with a minimally invasive approach. Operative morbidity and mortality in this population is due to the number of comorbidities present and the magnitude of obesity. Many complications involve the incision, anastomoses, staple lines, or the effects of general anesthesia or long-term problems due to patient non-compliance or self-destructing behaviors which may lead to weight gain and other nutritional derangements.

The second most popular operation performed in the United States and the most common weight loss procedure performed outside of the U.S. is a laparoscopically placed Lap Band. During this procedure an inflatable silicon band is placed around the stomach to create a small gastric pouch (15-20 cc). This operation imparts a feeling of early satiety and portion control to the patients by restricting the amount of food they can eat at one time. The band is adjustable to weight loss and restrictive symptoms and reversible. It is placed laparoscopically with short operating room times, low morbidity, and short hospital stays. However, these patients still require general anesthetic and can have a less than ten percent reoperation rate related to band slippage, erosion, or other mechanical failure. Often, reoperations are done laparoscopically but require general anesthesia as well.

Because of the use of general anesthetic and incisions to effect many conventional gastric bypass or reduction procedures, most patients require some recuperative stay in a hospital. Furthermore, any surgical procedure wherein an incision is made increases the risk of post-operative infection. It would, therefore, be beneficial and desirous to create a method of treating obesity in those persons having an overweight condition effectively without surgery. It would also be advantageous to provide an apparatus which facilitates the gastric reduction in a quick and cost effective manner. It would also be desirable to provide a treatment technique that is reversible in order to return a successful patient to a natural metabolic state.

SUMMARY OF THE INVENTION

In a broad aspect, there is provided herein an apparatus for creating a constriction in an opening. In a particular aspect, there is provided herein a method and apparatus for creating a stoma of a variable and reproducible size in a hollow organ. In particular, this invention relates to an improved method for creating a stoma of variable and reproducible size and an associated gastric pouch of variable and reproducible size within the stomach for the medical treatment of obesity or for cosmetic weight control.

This invention further relates to an apparatus for constraining and attaching an organ to an interior body cavity, to another organ, or to another suitable position in order to reposition the organ and provide support. This invention further relates to the treatment of obesity without the use of incisions. This invention further provides an implantable binding mechanism which is removable without surgical incision procedures or which produces a reversible effect, during a course of treatment. The implantation of the binding mechanism may be intended as a permanent appliance, fitted to a patient for life, or may be a temporary implant, being either removable through physical means, bio-resorptive means, or biodegradable means. This invention further relates to an apparatus for treating obesity, preferably in humans, which is noninvasive and provides for minimal discomfort and minimal recovery times. Additionally, in the implantation procedure the administration of general anesthesia may be eliminated.

In a particular aspect, there is provided herein an apparatus for constricting an opening without necessitating a surgical incision in order to access an outer surface of an organ lumen. Additionally, this invention contemplates a method and apparatus for creating a stoma of an adjustably variable size, having a range of adjustment, during its implanted use. This invention further contemplates a method and apparatus for removing a binding mechanism, a stricture device, stoma forming structure or device, and a stoma created without surgical incision procedures. The implant of this invention may be intended as a permanent appliance, fitted to a patient for life, or may be a temporary implant, being either removable through physical, bio-resorptive, or biodegradable processes.

In certain embodiment, the temporary nature of the implantation of the binding mechanism, as described herein, can relate to the weight loss objectives of the patient, whether medically or cosmetically motivated. The temporary nature of the implantation of the binding mechanism can also relate to the size of gastric pouch or lumen, and the attendant stoma that are created which is impacted by a patient's desired or mandated life style changes. Temporary may be defined, for purposes of this invention, as a length of time spanning treatment using the implantation of the binding mechanism, regardless of the motivation for use, that is shorter than the patient's remaining lifetime.

Though described in detailed relation to bariatric procedures, this invention is also applicable to other procedures which require surgical access to an organ lumen. Furthermore, this method and apparatus are applicable to forming a pre-sized stoma anywhere along a gastro-intestinal tract or resizing an existing stoma. For instance, this method is applicable to various anchoring surgical methods in order to constrain an organ, such as a stomach, to an interior wall of an abdominal cavity, as in the reduction treatment of a paraesophageal hernia. Further, this procedure may find equal use in constricting a lumen to prevent passage of matter therethrough, such as in various contraceptive techniques. An example of such a technique would be tubal ligation, wherein a woman's fallopian tubes are disrupted or constricted to prevent passage of an egg toward the uterus, thus resulting in sterilization.

As a further aspect of the invention, the method and apparatus are suitable to create an anastomosis between two segments of a hollow organ, such as a bowel or intestinal tract, or between two hollow organs. The method and apparatus may alternatively be used to juxtapose two organs or segments thereof in a relative and fixed orientation, either temporary or permanent. The method and apparatus of the invention are also useful for creating a stomatic area to treat gastro-esophageal reflux disease, as part of an anti-reflux procedure.

The invention further has applicability in placement of a removable stent in the gastro-intestinal tract. The stent can be deployed within the bowel wall rather than intralumenally within the bowel cavity. Additionally, control of fecal incontinence may be achieved by applying the method and apparatus of the invention to the rectum. Reduction of a sigmoid or cecal volvulus treatment, treatment of any bowel stricture, and even construction of a feeding tube and anchoring the tube to an abdominal wall may also be achieved. The above applications are not intended to be an exhaustive listing nor limit the other varied and useful applications of this invention to other surgical procedures.

Various objects and advantages of this invention will become apparent to those skilled in the art from the following detailed description of the preferred embodiment, when read in light of the accompanying drawings.

BRIEF DESCRIPTION OF THE DRAWINGS

FIG. 2 is a view similar to FIG. 1, showing the inner stomach cavity being sealed off by the endolumenal restriction apparatus.

FIG. 3A is a view similar to FIG. 1, showing the contracted stomach cavity.

FIG. 3B is a view similar to FIG. 3 showing the contracted stomach cavity with another embodiment of the endolumenal restriction apparatus.

FIG. 4 is an enlarged elevational view in cross section of a part of the endolumenal gastric apparatus of FIG. 3, illustrating deployment of a binding mechanism into and circumferentially around a constricted section of the stomach organ.

FIG. 6 is an elevational view in cross section of a stomach organ having a small gastric pouch and stoma.

FIG. 7 is a partial cross sectional view of a small gastric pouch and stoma made in accordance with an alternative embodiment.

FIG. 8 is an exploded elevational view of one embodiment of an endolumenal restriction apparatus.

FIG. 9 is an enlarged exploded perspective partial view shown the relation of a tissue collection member to the endolumenal restriction apparatus.

FIG. 9A is an enlarged perspective view of a portion of another embodiment of the suction chamber assembly of FIG. 9.

FIG. 10 is an enlarged partial view of a deployment mechanism loaded with a coil binding mechanism and disposed within a portion of the endolumenal restriction apparatus of FIG. 8.

FIG. 11 is a schematic representation of the deployment action of the deployment mechanism of the invention.

FIG. 12 is an enlarged partial view of the deployment mechanism after deployment of the coil binding mechanism.

FIG. 17 is a perspective elevational view of an alternative embodiment of a coil binding mechanism.

FIG. 18 is a perspective elevational view of an alternative embodiment of the coil binding mechanism of FIG. 17.

FIG. 19 is a perspective elevational view of an alternative embodiment of a coil binding mechanism.

FIG. 20 is a perspective elevational view of an alternative embodiment of a coil binding mechanism of FIG. 19.

FIG. 21A is a perspective elevational view of an embodiment of a ring binding mechanism.

FIG. 21B is a perspective elevational view of another embodiment of a ring binding mechanism.

FIG. 22A is a perspective elevational view of an embodiment of a restriction apparatus.

FIG. 22B is a perspective elevational view of an alternative embodiment of a restriction apparatus.

FIG. 22C is a partial cross sectional view of a small gastric pouch and stoma made in accordance with an alternative embodiment.

FIG. 22D is an enlarged, end view of the restriction apparatus taken along line 22D in FIG. 22C.

FIG. 22E is an enlarged, end view of the restriction apparatus taken along line 22E in FIG. 72C.

FIG. 22G is an enlarged perspective view of an alternative embodiment of the ring binding mechanism, shown in an unclamped position.

FIG. 24A is an enlarged, elevational view in partial cross section of an embodiment of a variable restriction apparatus in a collapsed position.

FIG. 24B is an enlarged, elevational view in partial cross section of a variable restriction apparatus in a deployed position.

FIG. 24C is an enlarged perspective view of an embodiment of a hinge element of FIG. 24B.

FIG. 25A is an enlarged, elevational view in partial cross section of an alternative embodiment of a variable restriction apparatus in a position prior to deployment.

FIG. 25B is an enlarged, elevational view of the articulating fin supports in a deployed position of the variable restriction apparatus of FIG. 25A.

FIG. 25C is an enlarged perspective view of an embodiment of a hinge element of FIG. 25B.

FIG. 26A is an enlarged, elevational view in partial cross section of an alternative embodiment of a variable restriction apparatus in a position prior to deployment.

FIG. 26B is an enlarged, elevational view of articulating fin supports in a deployed position of the variable restriction apparatus of FIG. 26A.

FIG. 26C is an enlarged perspective view of an embodiment of a hinge element of FIG. 26B.

FIG. 28 is an enlarged view, partially in phantom, of a portion of an endolumenal restriction removal apparatus with a hood structure in an insertion condition.

FIG. 29 is an enlarged view, partially in phantom, of a portion of the endolumenal restriction removal apparatus of FIG. 28 with the hood structure in a removal condition.

FIG. 30 is an enlarged view, partially in phantom, of a portion of an endolumenal restriction removal apparatus of FIG. 29 with the hood structure in an extraction condition.

FIG. 31 is an enlarged, end view of a removal cylinder portion of the endolumenal restriction removal apparatus of FIG. 29.

FIG. 32 is an enlarged, perspective view of the removal cylinder of FIG. 31.

DETAILED DESCRIPTION OF THE PREFERRED EMBODIMENT

Figure 1:
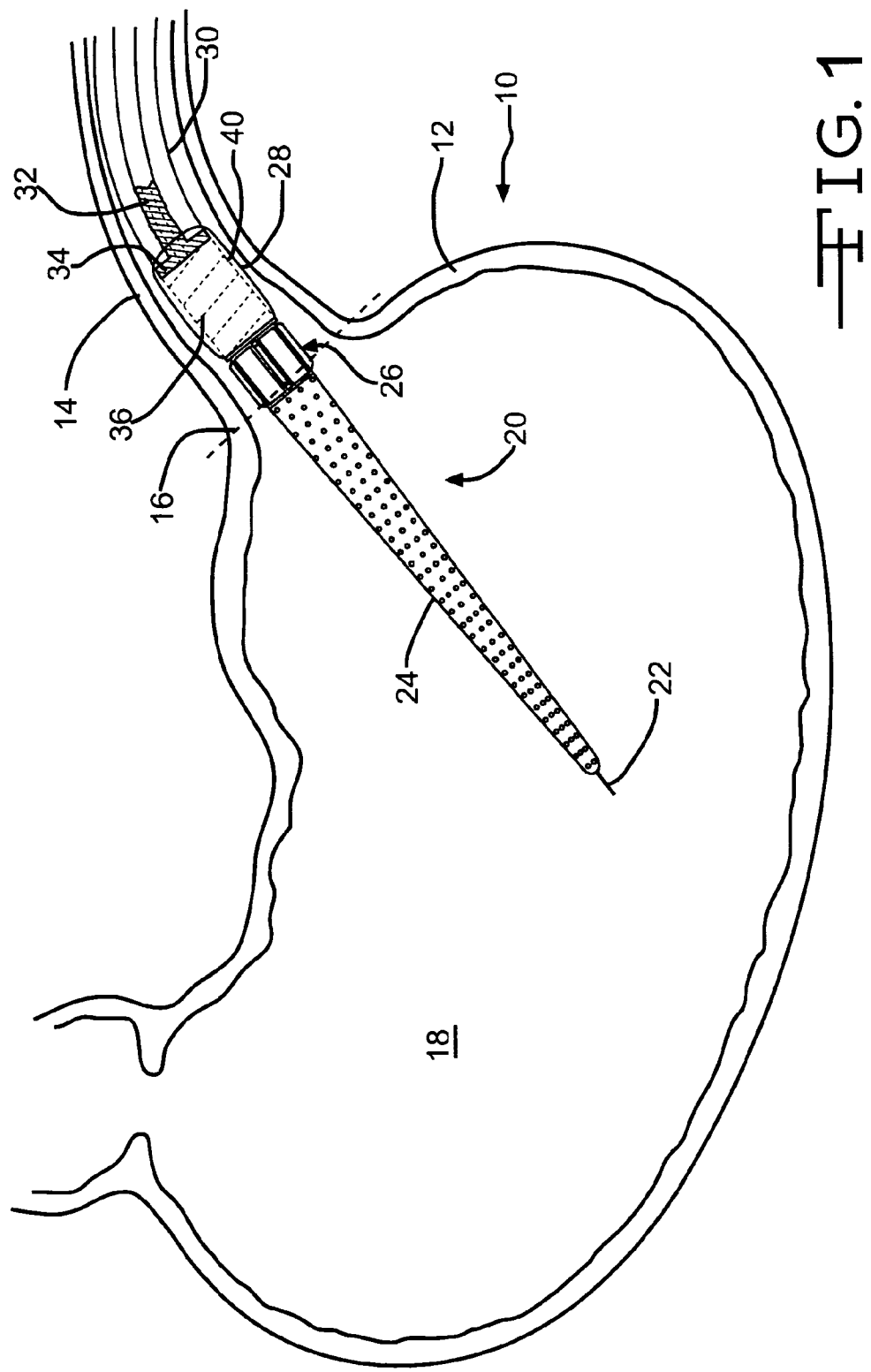
FIG. 1 is a front elevational view, partially in cross section, of an endolumenal restriction apparatus inserted into a human stomach.

Referring now to the drawings, there is illustrated in FIG. 1 a section of a gastro-esophageal portion of a digestive tract, indicated generally at 10. The digestive tract portion 10 is illustrated to represent a human stomach 12, having an internal cavity 18, and an esophagus 14. The illustrated digestive tract 10 further includes a gastro-esophageal junction 16. The stomach 12 and attendant digestive tract is preferably one where bariatric treatment may be deemed necessary, however this invention has equal applicability to patients desiring cosmetically motivated treatment. The method and apparatus described herein however, as will be readily apparent, may be applicable to other hollow or tubular organs necessitating a restrictive passage or closure therein. Furthermore, the method and apparatus may be equally applicable to other surgical procedures wherein an organ, having an accessible cavity, may be fixed to another section of the body, such as a stomach anchored to an internal abdominal wall. This invention may be further applicable to similar procedures conducted on any suitable species' internal organs, for example a digestive system or a portion of a reproductive system.

As illustrated in FIG. 1, an endolumenal restriction (ER) apparatus, indicated generally at 20, is shown during an insertion stage where a binding mechanism 36 is being implanted in a patient's stomach. An endoscope (not shown) can be used initially to insert a guide wire 22 into the stomach 12 through the patient's mouth. After the guide wire 22 is positioned from outside of the mouth through to the stomach cavity 18, the endoscope is removed. The ER apparatus 20 is threaded over the guide wire 22 and passed through the mouth (not shown) and the esophagus 14 into the stomach 12, as illustrated in FIGS. 1 and 2. It should be understood that the mouth or oral cavity is described for illustrative purposes only and is not a limiting disclosure. The ER apparatus 20, and apparatuses used in the endoscopic procedure, may be inserted into any natural body opening, such as for example, the stomach, an esophagus, an intestinal tract, the fallopian tube, the vagina, the rectum, the urethra, the ureter, the penile meatus, any bronchial passageway, the nares, and the like in order to access the appropriate organ cavity.

Thus, a first broad aspect, there is provided herein an endolumenal restriction apparatus 20 for creating a restriction in a tissue. The endolumenal restriction apparatus 20 generally includes a tissue collection member 26 (or, in certain embodiments, 37, 137, 237) that defines an interior space. The tissue collection member 26 (or 37, 137, 237) is configured to outwardly support at least one portion of the tissue and to allow at least a different portion of tissue to enter the interior space. The tissue is at least partially gathered in the interior space. The endolumenal apparatus 20 also includes a deployment mechanism that is configured: i) to insert a binding mechanism 36 (or, in certain embodiments, 80) into the gathered tissue, and ii) to position the binding mechanism 36 (or 80) in engagement with the gathered tissue to bind the gathered tissue.

In another broad aspect, the endolumenal restriction apparatus 20 is useful for creating a restriction in a tissue. The endolumenal restriction apparatus 20 includes a lumen sizing structure 28, a tissue collection member 26, or, in certain embodiments, 37, 137, 237) and a deployment mechanism for inserting the binding mechanism 36 (or in certain embodiments, 80). Generally, the lumen sizing structure 28 is configured to define a size of a lumen formed from a first portion of the tissue. The tissue collection member 26 is configured to be position at least adjacent to the lumen. The tissue collection member 26 generally defines an interior space such that the tissue collection member outwardly supports at least a second portion of tissue and allows at least a third portion of tissue to enter the interior space.

The deployment mechanism is generally configured to insert a binding mechanism into the gathered tissue while maintaining the stoma, and to position the binding mechanism in engagement with the gathered tissue to bind the gathered tissue, thereby maintaining the defined size of the lumen.

In certain embodiment, the third portion of tissue comprises gathered tissue such that the gathered tissue defining a stoma through which matter may pass.

Also, in certain embodiments, the endolumenal apparatus is configured to be endoscopically inserted into a patient. The binding mechanism can be configured to be removable from the gathered tissue.

Referring again to the Figures, in certain embodiments, the lumen sizing structure 28 is operatively connected to an outer tube 30 and a hollow, inner suction tube 32 passing therethrough. The outer tube 30 and inner suction tube 32 can be made from a flexible material, such as a plastic suitable for surgical applications. The outer tube 30 may be provided with calibrated markings (not shown) or other indicia suitable to determine the length that the ER apparatus 20 that has been inserted into the patient. The calibrated markings allow for an accurate positioning within the stomach relative to a datum point on the patient, such as the incisors. The outer tube 30 terminates at a lumen sizing structure 28 adapted to define the size of an lumen, such as for example a gastric pouch 52, that is a smaller size formed from a portion of the larger organ cavity.

The lumen sizing structure 28 may be defined, for the purpose of describing the scope of this invention, as any device, inflatable or otherwise, rigid or flexible, that is capable of expanding in an outward direction to create an enlarged cavity.

In certain embodiments, the lumen sizing structure 28 may be an inflatable or expandable balloon type structure, as shown in FIGS. 1-4A. In one non-limiting embodiment, the lumen sizing structure 28 may be a balloon structure of a construction similar to that disclosed in U.S. Pat. No. 5,545,179 to Williamson which is expressly incorporated herein by reference in entirety. The description of the sizing structure as an inflatable balloon type lumen sizing structure 28 is not intended to exclude other sizing elements or be a limiting disclosure in any way, but is merely a description of an embodiment of the invention.

Figure 4A:
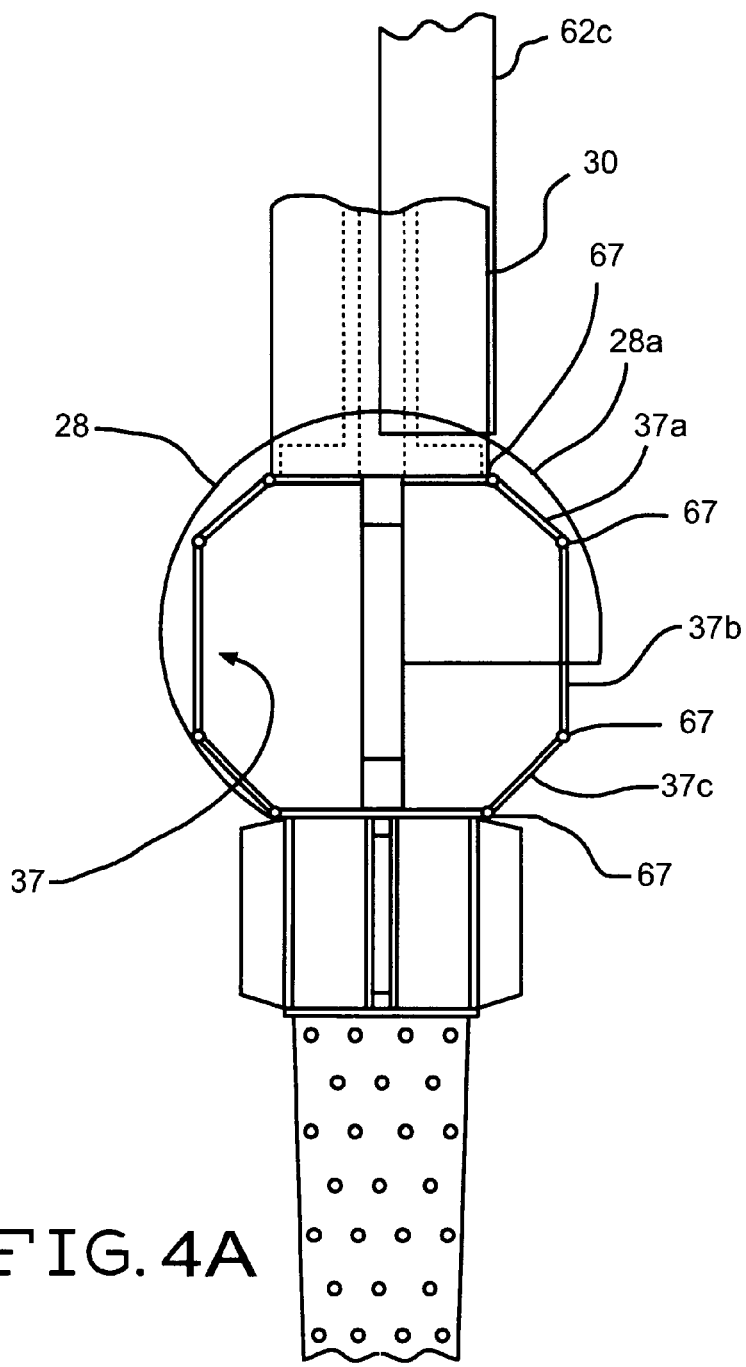
FIG. 4A is an enlarged elevational view in cross section of a part of another embodiment of an endolumenal restriction apparatus.

In another embodiment, the lumen sizing structure 28 may include mechanical expansion structures, such as for example an expandable cage structure, shown generally at 37 in FIG. 4A. The expandable cage structure 37 may include a plurality of radially extending or radially pivotable arms 37a, 37b, and 37c. The radially extendable arms 37a, 37b, and 37c may be more or less in number than shown. The radially extendable arms 37a, 37b, and 37c may further be shaped as straight sections or fingers, or curved surfaces that resemble spoons (not shown) or the like which are structures capable of outwardly orienting tissue to structure a cavity or gastric pouch 52. The radially extendable arms 37a, 37b, and 37c may further include hinges, thinned sections, flexible material segments, and the like to facilitate articulation as described below in detail.

Figure 27A:
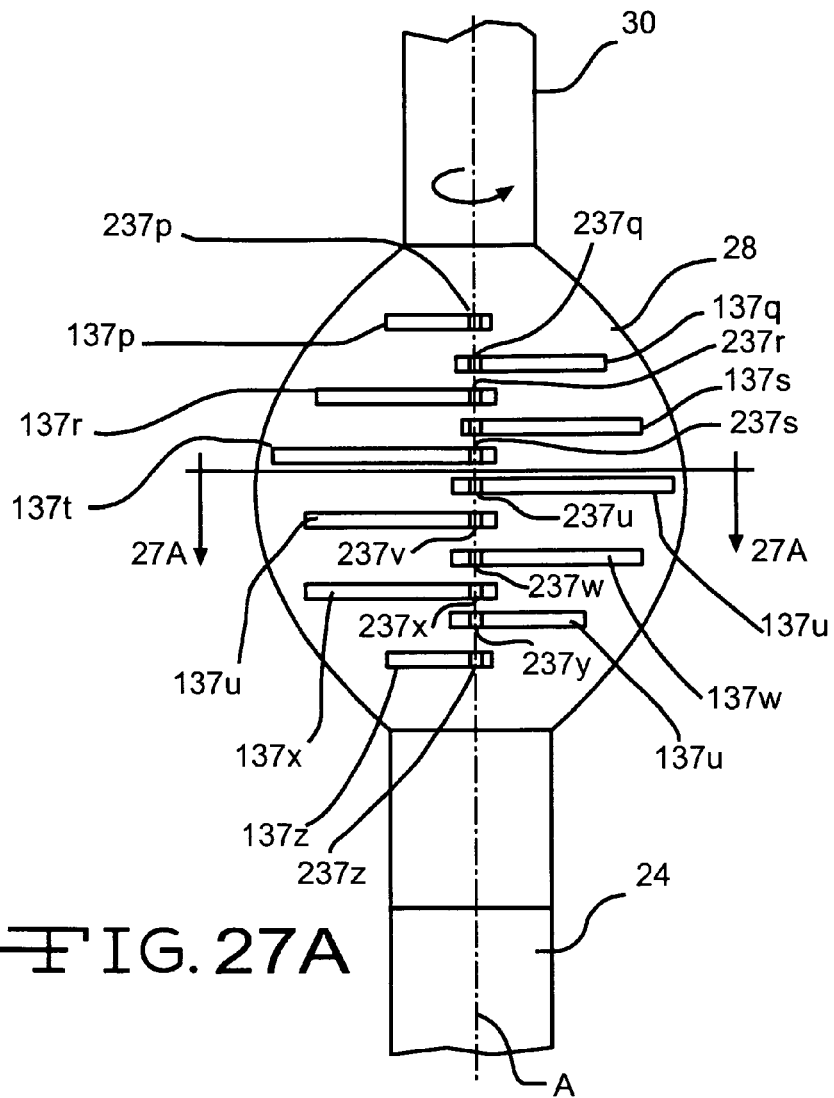
FIG. 27A is an enlarged, cross sectional view of an alternative embodiment of a balloon type lumen sizing structure.
Figure 27B:
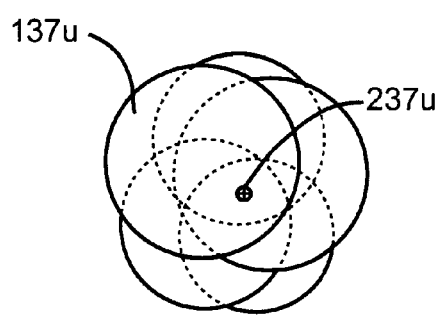
FIG. 27B is a cross sectional, end view of the sizing structure of FIG. 27A.

In yet another embodiment, as shown in FIGS. 27A and 27B, the mechanical expansion structures may be a plurality of radially extending disks 137p-137z, or a camera aperture-like structure (not shown) and the like. The radially extending discs 137 may be a series of pivotable elements 137p-137z (for example, having a generally circular or elliptical shape) that may be oriented in a plane that is substantially perpendicular to the walls of the gastric pouch 52. The discs 137p-127z may be configured as solid disc structures; narrow, arcuate sections having a circular or elliptical contour; or may be solid structures having an aperture 237p-237z formed through each disc 137p-137z, respectively. The apertures 237p-237z may be spaced such that they are aligned sufficiently to pass a surgical element therethrough when the discs are deployed to create the cavity. The radially extending discs 137p-137z may be radially disposed from a central axis or series of axes (not shown) in order to create the cavity or gastric pouch 52 for the purposes described herein.

Referring again to FIGS. 1-4, the lumen sizing structure 28 may be an articulable, radially expandable and contractible device that is analogous to the structure of a camera lens aperture (not shown).

Also, in certain embodiments, the lumen sizing structure 28 that articulates to expand, rather than inflate, may have the outer layer or flexible covering to completely cover the articulating cage 37 in FIG. 4A, and may be attached to, or as an integral part of, the outer tube 30. In an embodiment of the invention, the lumen sizing structure 28 may be a balloon type structure that completely encapsulates the articulating cage 37. Alternatively, a hooded structure 28a may be configured in an analogous manner to an umbrella and may shield the expandable cage 37. The balloon type lumen sizing structure 28 and the hooded lumen sizing structure 28a may facilitate insertion and removal of the ER apparatus 20, protect the esophagus from abrasion, and provide a sealing mechanism to close off the stomach cavity 18 from the esophagus in order to support the tissues adjacent to the formed restriction. The support facilitates installation of the binding mechanism into the formed restriction.

FIG. 2 shows the ER apparatus 20 positioned at the gastro-esophageal junction 16. Prior to expansion or inflation, the ER apparatus 20 is inserted into the stomach cavity 18 a sufficient distance to allow the balloon type lumen sizing structure 28 to be positioned and inflated within the stomach cavity 18. The positioning and final location of the ER apparatus 20 relative to the gastro-esophageal junction 16 and the inflation size of the balloon type lumen sizing structure 28 are determined by the clinical judgment of the treating physician. Examples of considerations affecting placement and inflation size determinations may include a diagnosis of the patient's condition, stomach size, and extent of treatment necessary to achieve the desired medical objectives, among other pertinent factors. Though illustrated as positioned in a location intersecting the gastro-esophageal junction 16, the balloon type lumen sizing structure 28 may be positioned other than illustrated based on medical judgment. For example, a patient's medical condition may dictate that the gastric pouch 52 (see FIGS. 6-7), which is to be formed by the balloon type lumen sizing structure 28, be formed below the gastro-esophageal line. This position may be selected to avoid interfering with or incorporating affected tissues, such as those affected with gastro-esophageal reflux disease (GERD) or Barrett's Esophagus, to minimize exposure to stomach contents.

Figure 16:
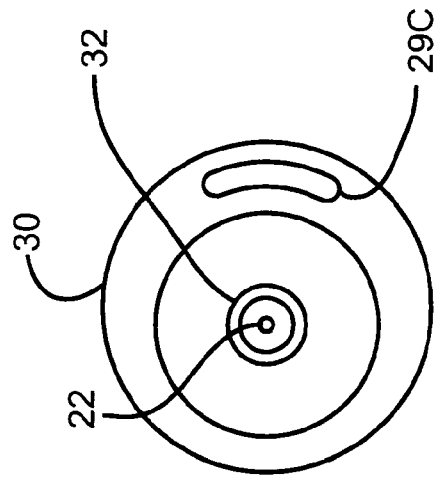
FIG. 16 is an enlarged, cross sectional view of an alternative embodiment of the outer tube, suction tube, guide wire, and inflation tube.
Figure 14:
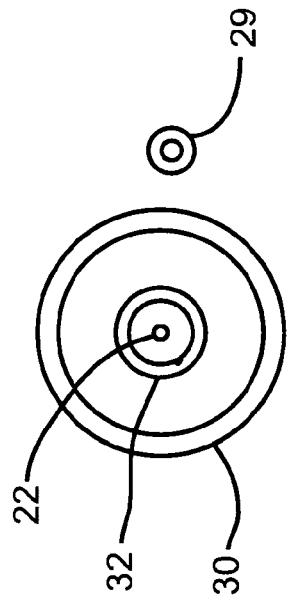
FIG. 14 is an enlarged, cross sectional view of an outer tube, suction tube, guide wire, and inflation tube taken along line 14-14 in FIG. 8.
Figure 15:
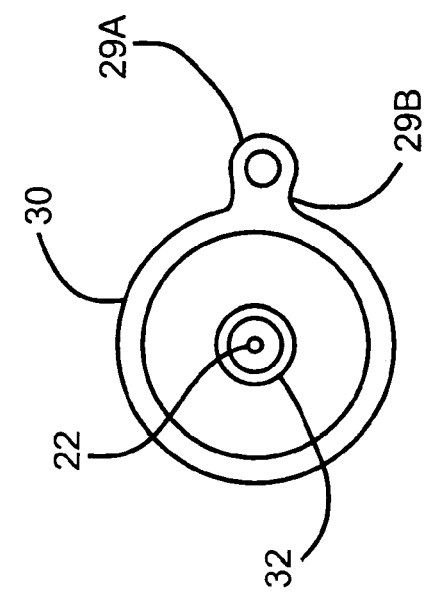
FIG. 15 is an enlarged, cross sectional view of another alternative embodiment of the outer tube, suction tube, guide wire, and inflation tube.

In certain embodiments, the balloon type lumen sizing structure 28 can be constructed of an expandable material such as, for example, silicone or latex rubber or any suitable material capable of contacting bodily fluids and being compatible with surrounding tissues. The expandable material is further capable of inflating or expanding from a size small enough to pass the ER apparatus 20 into an organ cavity to a size sufficient to create a desired cavity in the stomach or other organ. The balloon type lumen sizing structure 28 may be inflated by an inflation tube structure 29 exterior to the outer tube 30, as shown in FIG. 8. The outer tube 30, with the coaxially disposed suction tube 32, the guide wire 22, and the inflation tube 29 are shown in FIG. 14. Although shown as being separated from the outer tube 30, the inflation tube 29 may be an integral part of the outer tube 30. FIG. 15 illustrates an alternative embodiment of a two tube co-extrusion of outer tube 30 and inflation tube 29A, connected together by a web 29B. FIG. 16 illustrates an alternative embodiment of a voided cavity 29C within a wall section of the outer tube 30. Therefore, associated with the outer tube 30 is an inflation tube structure 29 operatively connected to the balloon type lumen sizing structure 28 and, alternatively, part of outer tube 30. The inflation tube structure 29 provides fluid communication between a fluid source, preferably external to the patient, and the balloon type lumen sizing structure 28. The fluid supplied by the inflation tube 29 to the balloon type lumen sizing structure 28 may be air, water, saline solution, or any applicable medium conducive to use in an operating environment and suitable for the intended inflation of the balloon type lumen sizing structure 28.

Alternatively, the inflation tube 29 may be defined as an articulation tube that is mechanically attached to the articulable sizing structure of the balloon type lumen sizing structure 28 in order to deploy the expandable cage 37 or other mechanical expansion structures described herein. The inflation tube 29 may be constructed as a hollow tube and positioned such that a rotational movement of the tube 29 actuates the balloon type lumen sizing structure 28. Once actuated, outwardly positioning the inner structure, such as the expandable cage 37, in a variable amount and degree may create a pouch of a variable size range with the ER apparatus 20.

The inflation tube 29 may be articulated in an axial direction, relative to the outer tube 30, or as part of the outer tube 30 itself, to deploy the flexible or pivotable portions of the balloon type lumen sizing structure 28. Alternatively, the inflation tube 29 may be a cable-like structure, or contain a cable-like structure, that is connected to the flexible or pivotable portions of the balloon type lumen sizing structure 28, or connected to a structure that connects to and deploys the balloon type lumen sizing structure 28. The inflation tube 29, either as a pneumatically-operated, fluid pressurized, or mechanically-operated device, also may retract the balloon structure 28 when desired.

The balloon type lumen sizing structure 28 may be inflated or expanded, in one embodiment, within the stomach cavity 18. After inflation or expansion, the balloon type lumen sizing structure 28 may be withdrawn to a point in proximity to the gastro-esophageal junction 16. The deployed balloon type lumen sizing structure 28 is positioned in order to seal off the esophagus 14 and support the tissues adjacent to the formed restriction. The support facilitates installation of the binding mechanism 36 into the formed restriction. Alternatively, the balloon type lumen sizing structure 28 may be partially inflated or expanded and withdrawn partially from the stomach to structure an initial seal, thus forming the gastric pouch 52 positioned further into the gastro-esophageal junction 16. The balloon type lumen sizing structure 28 is inflated or expanded to a size based on appropriate medical indications to create the gastric pouch 52, as shown in FIGS. 6 and 7. The balloon type lumen sizing structure 28, as a mechanically operated structure, and the hood structure 28a, shown in FIG. 4A, may be partially deployed and positioned, as described above.

In certain embodiments, the size of the gastric pouch 52 may be in a range of about 15-30 cubic centimeters. The gastric pouch 52 may be sized greater or smaller than indicated, however, and remain within the scope of the invention. For example, gastric pouch volumetric ranges of 10 to 50 cubic centimeters or 30 to 100 cubic centimeters may be indicated by medical judgment. Once inflated or expanded and pulled into position, for example near the gastro-esophageal junction 16, the balloon type lumen sizing structure 28 contacts the inner lining of the stomach 12 and/or esophagus 14 and creates a resistance to further extraction from the stomach cavity 18. This resistance provides an additional confirmation, along with the markings of the outer tube 30, to signal that the ER apparatus 20 is at or near the desired area, i.e. at the gastro-esophageal junction 16.

Once the balloon type lumen sizing structure 28 is inflated or expanded to the appropriate size and located into the proper position, the ER apparatus 20 may be operatively connected to a suction device (not shown) or other vacuum drawing apparatus in order to draw tissue inwardly forming the restriction and to support the tissues adjacent to the formed restriction. The support facilitates installation of the binding mechanism into the formed restriction, as shown in FIG. 3A. It may be advantageous in some cases to evacuate at least a portion of the contents of the stomach cavity 18, though such is not required. In an alternative embodiment of the ER apparatus 20 shown in FIG. 3B, a tissue stabilizer 24a can be provided in place of the perforated suction tip 24. The tissue stabilizer 24a is an inflatable or expandable structure that provides a foundation for drawn-in tissue. The wall tissue of the stomach 12 is supported by the tissue stabilizer 24a so that various embodiments of a suitable binding mechanism 36, as will be described below, may positioned to create a stoma therein. Alternatively, the stomach contents may not be evacuated and the ER apparatus 20 may not require the use of vacuum to perform an evacuation of any such organ cavity contents.

Figure 13:
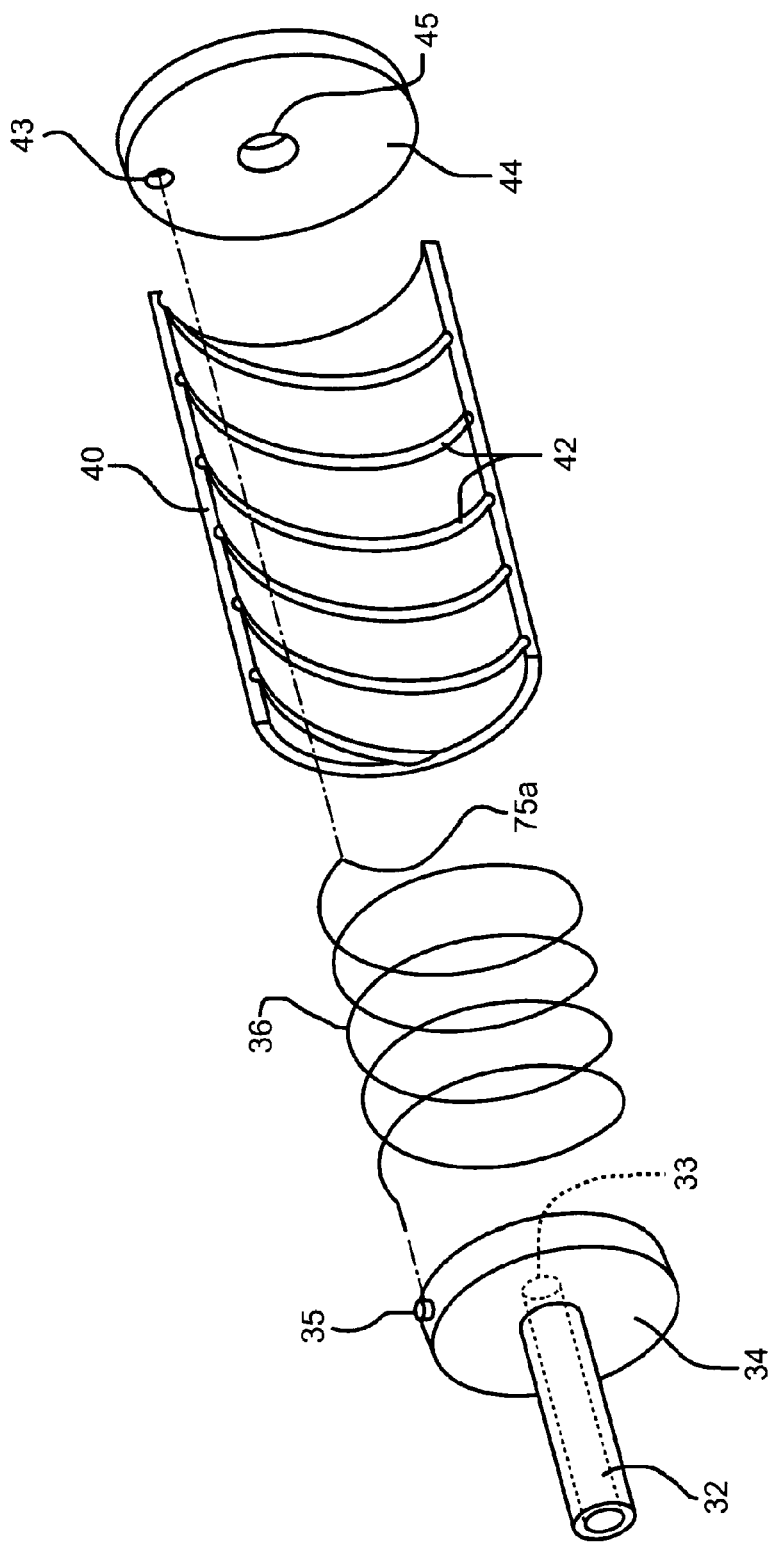
FIG. 13 is an enlarged, exploded, perspective view, in partial cross section, of the coil deployment mechanism of FIG. 10.

The ER apparatus 20 may be connected to a suction device (not shown) through the suction tube 32. The suction tube 32 terminates in a piston 34 having an aperture 33 formed therethrough, as shown in FIGS. 8 and 13. Though described as separate components, the piston 34 and the suction tube 32 may be integrally formed as a single structure.

The suction tube 32 is in fluid communication with a perforated suction tube, shown generally at 46 in FIG. 8, that includes a perforated portion 47, a non-perforated portion 48, and a guide wire aperture 49. The perforated portion 47 includes a first perforated section 47a having larger holes that are aligned generally with a tissue collection member 26, such as a suction port, to draw tissue within a plurality of openings 25, illustrated in FIGS. 4 and 8. The perforated portion 47 further includes a second perforated section 47*b* including a plurality of smaller holes that are aligned generally with a perforated tip 24.

The description of the tissue collection member 26 as a vacuum actuated and structurally static suction port device is not intended to exclude other sizing and stoma creating elements or be a limiting disclosure in any way, but is merely a description of an embodiment of the invention. Alternatively, the tissue collection member 26 may be defined as any structure having the ability to draw or gather at least a portion of tissue from a first position and move the portion of tissue to a second position that is radially interior to the first position. Further, the tissue collection member 26 may not need to operate by vacuum or any other negative pressure source. Alternatively, the tissue collection member 26 may be a mechanically operated device having fingers or hooks (not shown) capable of pinching, grabbing, snagging, or piercing the tissue desired to be drawn toward the center of the ER apparatus 20 and intended to create a stoma 54 or any other restriction or constriction of an organ, opening, or tubular passageway.

The balloon type lumen sizing structure 28 and the tissue collection member 26 may be independently sized and combined such that various stoma 54 and gastric pouch 52 configurations may be created. For example, the ER apparatus 20 may include a balloon type lumen sizing structure 28 that is sized to create an approximately 20 cc gastric pouch.

The tissue collection member 26 may be sized to produce a stoma 54 that may range from 12-15 mm, or larger depending on the desired result. Other stoma and gastric pouch size configurations may also be achieved depending on the proposed diet and weight loss rate indicated. A patient desiring a reduced weight loss rate with minimal dietary changes may benefit from a larger gastric pouch size. For example, a 30 cc gastric pouch may include an 18-21 mm stoma size, though larger or smaller stoma sizes may be used.

Referring again in particular to FIG. 8, the aperture 33 of the piston 34 may be attached to the perforated suction tube 46 to provide fluid communication between the perforated suction tube 46 and the external vacuum source. The aperture 33 and the associated suction tube 32 may engage the non-perforated portion 48 of the perforated suction tube 46 in an interference fit relationship or a close-fitting, sliding relationship.

Alternatively, the suction tube 32, piston 34, and perforated suction tube 46 may be formed as an integral structure, either by molding them as such, or by assembling the components using adhesive bonding, thermal welding, chemical welding, snap-fit assembling and the like. In another embodiment, the suction tube 32, the piston 34, and the perforated suction tube 46 may be an integral, singular structure. Whether a singular structure or an assembly of several pieces, the suction tube 32, the piston 34, and the perforated suction tube 46 cooperate to provide fluid communication between the vacuum source and the stomach cavity 18.

The tissue collection member 26 may be in fluid communication with the perforated suction tube 46 through alignment of perforated section 47*a*, as illustrated in FIG. 8.

In certain embodiment, the ER apparatus 20 generally includes a deployment mechanism 40 (such as a chamber 40 described below) for receiving the binding mechanism 36 and an advancing device (such as a piston 34) disposed between the tissue collection member and the coil chamber for advancing the binding mechanism into the gathered tissue.

In the embodiment shown in FIGS. 8 and 13, the ER apparatus 20 includes a binding mechanism deployment mechanism that includes a coil chamber 40 located at or near the end of the outer tube 30 and interior to the balloon type lumen sizing structure 28. A barrier disc 44 is disposed between the tissue collection member 26 and the coil chamber 40. The barrier disc 44 includes a center aperture 45 and a coil deployment aperture 43, best seen in FIGS. 9 and 13. The center aperture 45 provides access for the perforated suction tube 46 to pass through to the center of the tissue collection member 26 and the perforated suction tip 24. The coil deployment aperture 43 provides an exit port for a binding mechanism 36 has a coil suture type structure when the coil type binding mechanism 36 is deployed from the coil chamber 40, as illustrated in FIG. 4. Though illustrated as a cylindrically shaped aperture, the coil deployment aperture 43 may be any shape which facilitates the deployment of the coil suture type binding mechanism 36 from the coil chamber 40 into the target tissue disposed about the tissue collection member 26. The coil deployment aperture 43 may be, for example, a frustum of a cone or a cylindrical aperture generally angled in the direction of travel of the coil suture type binding mechanism 36 as it is deployed.

Referring again to FIG. 4, the coil chamber 40 includes a helical groove 42 having at least one turn and, preferably, a plurality of turns. The groove 42 is formed into the inner surface of the coil chamber 40 and locates or guides the coil suture type binding mechanism 36. The coil chamber 40 can be formed of a medical grade plastic similar to the outer tube 30, though other plastic and non-plastic materials may be equally suited substitutes. The coil chamber 40, however, may be more rigid than the outer tube 30 so that the coil suture type binding mechanism 36 is securely loaded and retained until deployed. A characteristic of the material forming the coil chamber 40 and the helical grooves 42, though not necessary to the general operation of the ER apparatus 20, is a relatively constant coefficient of friction between the coil suture type binding mechanism 36 and the helical grooves 42. The relatively constant coefficient of friction is preferably operative between a starting action of deployment of the coil suture type binding mechanism 36 and a running condition during deployment of the coil suture type binding mechanism 36. The relatively constant coefficient of friction, intended to minimize a "stiction" phenomenon, provides a smooth dispensing action of the coil suture type binding mechanism 36 into a target tissue such as, for example, the stomach 12.

In an alternative embodiment, the coil chamber 40 may be formed as an integral part of the outer tube 30 and contain the helical grooves 42 either for a discrete length or along the entire length of the outer tube 30 inner wall surface, if so desired for manufacturability. In this alternative embodiment of the coil chamber 40, a reinforcing sleeve member (not shown) of a stiffer material formulation may be disposed between the coil chamber outer diameter and the inner surface of the balloon type lumen sizing structure 28 to provide stiffness and support for the coil chamber 40, if so desired though such is not required.

The helical grooves 42, formed within the interior surface of the coil chamber 40, are preferably sized to securely locate or guide the coil suture type binding mechanism 36, as illustrated in FIGS. 4 and 10. In one embodiment, the coil suture type binding mechanism 36 is preferably made from a shape memory metal, such as Nitinol® or any other alloys suitable for surgical suture applications, which are known in the art. Other metal alloys suitable for surgical applications, though not possessing a shape memory characteristic, may also be used to construct the coil suture type binding mechanism 36.

The coil sutures 36 utilizing materials such as Nitinol®, stainless steel, composites and the like that are resistive to biological degradation may be intended for either permanent or temporary installation. The temporary coil suture installation is facilitated by a removal procedure discussed below. An alternative embodiment of the coil suture type binding mechanism 36 utilizes a biodegradable material such as Vicryl® suture or similar time sensitive suture materials. These biodegradable coil sutures may be deployed in the same manner as those coil sutures made from non-degradable materials as described above.

The coil suture type binding mechanism 36 may be of any size, shape, or configuration suitable for the purpose of binding the tissue gathered at the tissue collection member 26. In certain embodiments, the binding mechanism 36 may be a coil suture type binding mechanism 36 having a single turn configuration resembling a helix, as shown in FIG. 19, or a plurality of turns resembling a screw thread, as shown in FIG. 20. The turns of the coil suture type binding mechanism 36 may be a constant outer diameter, though tapering diameters from larger to smaller or smaller to larger may be provided.

In another embodiment, the binding mechanism 36 may be a banded structure, similar to the structures of FIGS. 21A-23 as described herein, and may have a cross sectional width larger than a cross sectional thickness. In another embodiment, the binding mechanism 36 may be a filamentary configuration or a thread-like structure. In yet another embodiment, the binding mechanism 36 may be a general binding structure such as adhesives, prongs, spikes, or staples.

The coil suture type binding mechanism 36 may be provided with a sharp end 75a, shown in FIGS. 4, 8, and 13, for piercing the tissue gathered around the tissue collection member 26 to create the stoma 54. The sharp, piercing end 75a may be positioned in the coil chamber 40 at the end proximal to the tissue collection member 26. FIGS. 17-20 illustrate alternative configurations of a piercing end 75b configured for use with an embodiment of a removal apparatus, as will be described below. The coil suture type binding mechanism 36 may have a blunt end proximal to the piston 34 to provide an assured contact with the piston 34 for positive deployment of the coil suture type binding mechanism 36. The coil suture type binding mechanism 36 may be provided with a turn diameter which is larger in the free state, outside of the coil chamber 40, than in the "as loaded" or wound up state within the coil chamber 40. Alternatively, the coil suture type binding mechanism 36 may be provided with a barbed surface 70, as shown in FIGS. 17 and 18. The barbed surface 70 of the coil suture type binding mechanism 36 may prevent the coil suture type binding mechanism 36 from becoming dislodged and assist in maintaining the coil suture type binding mechanism 36 in contact with the tissue.

The coil suture type binding mechanism 36 is deployed from the coil chamber 40 by rotation of the piston 34, as illustrated in FIGS. 4 and 10-12. The outer diameter surface of the piston 34 engages the inner wall of the coil chamber 40. The piston 34 includes a deployment nib 35 which is illustrated in FIG. 13. When the ER apparatus 20 is being "loaded", the piston 34 is rotated relative to the coil chamber 40 so that the deployment nib 35 engages the helical groove 42. The piston 34 is further rotated relative to the coil chamber 40 so that the deployment nib 35 follows a path defined by the helical groove 42. The piston 34 is screwed into the empty coil chamber 40 until a sufficient distance is reached to install the coil suture type binding mechanism 36. The coil suture type binding mechanism 36 is then oriented so that the blunt end is introduced first into the helical groove 42 at the end of the coil chamber 40 that is distal to the outer tube 30. The coil suture type binding mechanism 36 is further rotated into the helical groove 42 until the coil suture type binding mechanism 36 is substantially contained within the coil chamber 40, as shown in FIGS. 1-3 and 10. The coil suture type binding mechanism 36 further is seated in the helical groove 42 with the deployment nib 35 located at a position between the outer tube 30 and the coil suture type binding mechanism 36 blunt end. The assembly steps of the ER apparatus 20 prior to use is for illustration purposes and would be understood by one of ordinary skill in the art as not limiting the use of the apparatus nor the limiting the resulting restriction structures.

The barrier disc 44 helps prevent air from flowing into the perforated suction tube 24 from the outer tube 30. By directing the flow of negative pressure, the barrier disc 44 improves the efficiency of evacuating any desired portion of the contents of the stomach cavity 18. This directing of negative pressure in the area of the tissue collection member 26 further improves the efficiency of drawing tissue within the openings 25. The barrier disc 44 further limits or restricts tissue and other bodily fluids from entering the coil chamber 40.

In an alternative embodiment of the invention, the binding mechanism 36 may be a ring or band 80a, either singularly or as at least two rings or bands 80a and 80b, as shown in FIG. 21A. The coil chamber 40 may omit the inclusion of the barrier disc 44, if so desired, or alternatively, the loading order or sequence of components within the coil chamber 40 may be other than depicted or described. The ring binding mechanisms 80a and 80b may be of a substantially continuous circumference as shown in FIG. 21A. Alternatively, the ring or band binding mechanisms may be constructed of a coil segment having an overlapping portion, such as the expandable ring binding mechanism 80c illustrated in FIG. 21B. The expandable ring binding mechanism 80c may also comprise a plurality of expandable rings 80c. The expandable ring binding mechanism 80c may provide a stoma 54 of adjustable size after deployment.

The ring binding mechanisms 80a, 80b, and 80c include a center aperture 89 and may further include removal barbs 82 to facilitate removal of the resulting stoma 54, as will be discussed below. The ring binding mechanisms 80a, 80b, and 80c may further include engineered break points or cleavage points 83 in order to provide an alternative removal mechanism, as will be described below. The ring binding mechanisms 80a, 80b, and 80c may further include sizing sleeves (not shown) that engage the center aperture to alter the size, shape, or other characteristic of the stoma 54. The sizing sleeves may engage the ring binding mechanism 80a in a snap fit relationship or compressed and re-expanded to capture the ring binding mechanism 80a, the ring binding mechanisms 80a, 80b, and 80c, or other stoma creating structure.

The ring binding mechanisms 80a, 80b, and 80c may be made from a shape memory metal, such as Nitinol®, a Nickel-Titanium shape memory alloy, or any other alloys suitable for surgical suture applications, which are known in the art. Other metal alloys suitable for surgical applications, though not possessing a shape memory characteristic, may also be used to construct the ring binding mechanisms 80a, 80b, and 80c. The ring binding mechanisms 80a, 80b, and 80c utilizing materials such as Nitinol® alloy, stainless steel, composites and the like that are resistive to biological degradation may be intended for either permanent or temporary installation. An alternative embodiment of the ring binding mechanisms 80a, 80b, and 80c utilizes a biodegradable material such as Vicryl® polyglactin 910 absorbable, synthetic braided suture material, or similar time sensitive suture materials. These biodegradable rings may be deployed in the same manner as the coil type binding mechanism 36. The expandable ring binding mechanism 80c may alternatively be made from a material that is capable of a sufficient degree of plastic deformation without fracturing to allow the center aperture 89 to be resized after deployment. To increase the size of the center aperture 89, an expandable structure, such as the balloon type lumen sizing structure 28, may be inserted and expanded outwardly. The overlapping ends of the expandable ring binding mechanism 80c may slide relatively as the balloon type lumen sizing structure 28 expands to open the center aperture 89. The expandable ring binding mechanism 80c may plastically deform such that the center aperture 89 substantially retains an enlarged size after the balloon type lumen sizing structure 28 is contracted and removed.

Figure 22F:
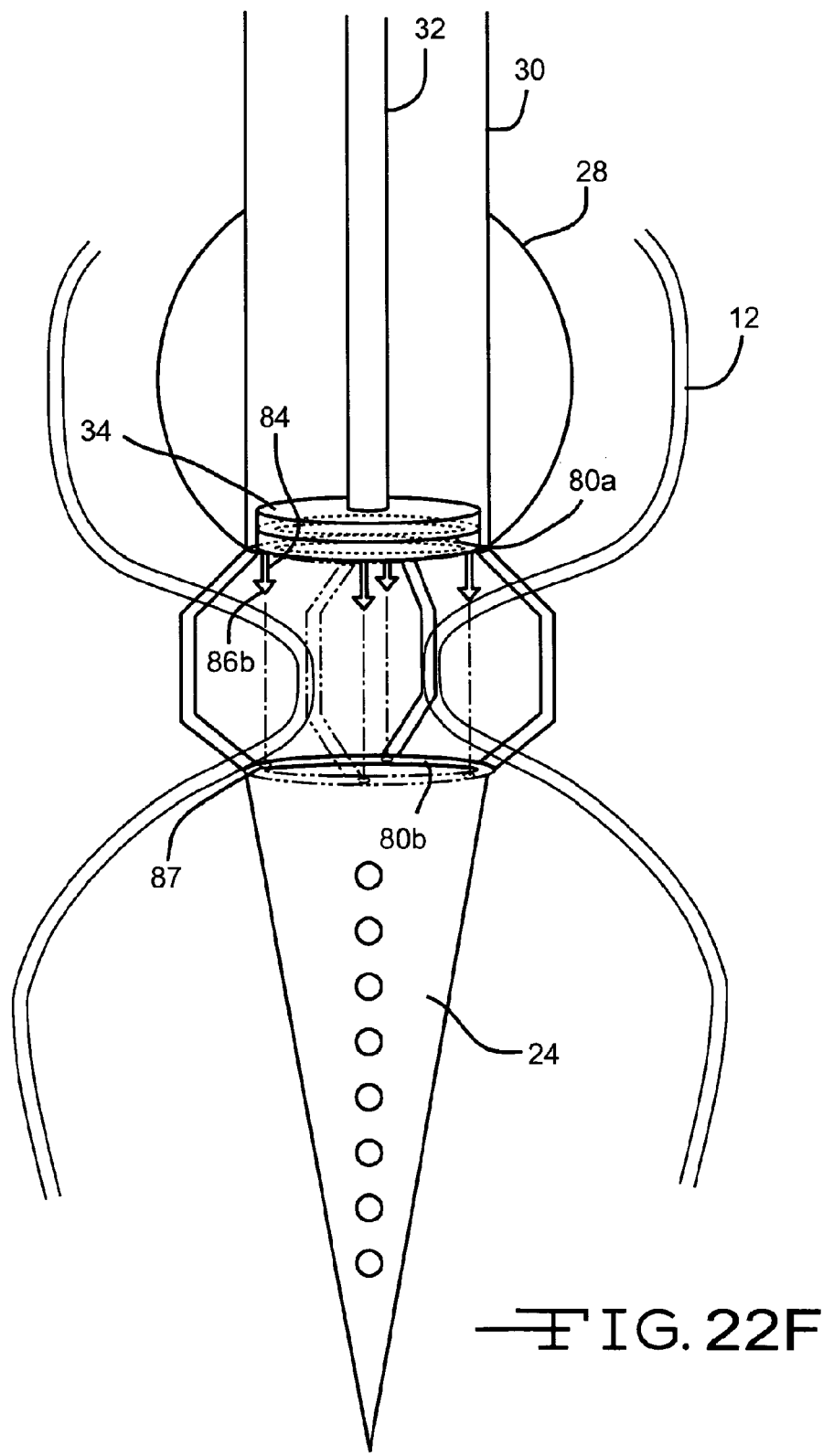
FIG. 22F is an enlarged, perspective view, in partial cross section and partially in phantom, of an alternative embodiment of a ring binding mechanism.
Figure 23:
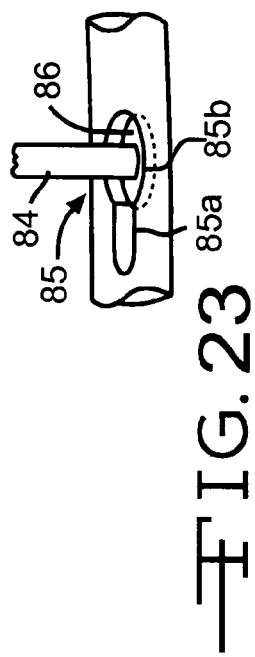
FIG. 23 is an enlarged, perspective view of a locking mechanism of the ring binding mechanism.
Figure 23A:
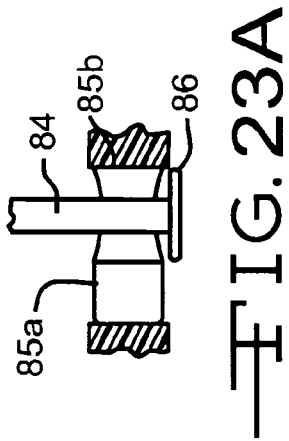
FIG. 23A is an enlarged view of the binding mechanism in an unlocked position.
Figure 23B:
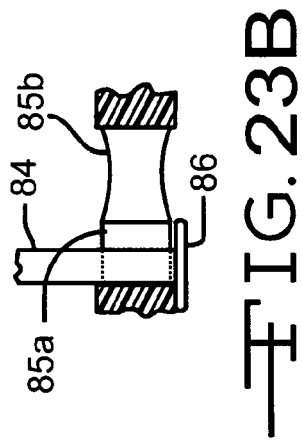
FIG. 23B is an enlarged view of the binding mechanism in a locked position.

FIG. 22A illustrates an alternative embodiment of a ring cage binding mechanism, indicated generally at 80, that includes the ring binding mechanisms 80a and 80b. The ring binding mechanisms 80a and 80b are spaced apart and connected together by a plurality of interconnecting members or legs 84. The interconnecting legs 84 may be provided to pierce through the gathered tissue, as illustrated in FIGS. 22B-22F. The interconnecting legs 84 include a first end 88, shown in FIGS. 22A and 22D, that is attached to the ring binding mechanism 80a. The first end 88 may be rigidly or pivotally connected to the ring binding mechanism 80a, or may be integrally formed therewith. Alternatively, the first end 88 may be attached to, or integrally formed with, the ring binding mechanism 80b or the expandable ring binding mechanism 80c. One embodiment of the leg 84 includes a second end that terminates in a locking feature, such as a button 86, shown in FIGS. 22E, 23, 23A, and 23B. The button 86 engages and passes through a loop aperture, shown generally at 85 in FIGS. 22A and 23-23B, as the ring binding mechanisms 80a and 80b are brought together and the interconnecting legs 84 have pierced through the gathered tissue, if so desired. The button 86 passes through the loop 85b such that the button 86 extends below the lower surface of the ring binding mechanism 80b. The ring binding mechanisms 80a and 80b may be rotated relative to one another so that the interconnecting legs 84 are moved along a slot section 85a and into a locked position, as shown in FIG. 23B.

FIGS. 22B and 22F illustrate alternative arrangements of the ring binding mechanisms 80a and 80b where the interconnecting legs 84 have embodiments of various retaining feature structures. The interconnecting legs 84 of FIG. 22B may have a terminating snap 86a that is slightly larger in diameter than a corresponding hole 87 in ring binding mechanism 80b. The terminating snap 86a may be pushed through the hole 87 such that, once through the gathered tissue, the interconnecting leg 84 is secured to the ring binding mechanism 80b. Alternatively, the end of interconnecting leg 84 may include a piercing barb 86b that engages the corresponding hole 87, as shown in FIG. 22F, in a locking relationship. The expandable ring binding mechanism 80c may be used in place of the ring binding mechanisms 80a and 80b and further created with the interconnecting and locking features as previously described, if so desired.

The ring binding mechanisms 80a and 80b, along with the interconnecting legs 84, may be used in place of the tissue collection member 26, if so desired. In this arrangement, the ring binding mechanism 80a and attached interconnecting legs 84 may be spaced apart from the ring binding mechanism 80b such that the gathered tissue is drawn toward the center of the ER apparatus 20 through the space between the ring binding mechanisms 80a and 80b. Further, some tissue may project between adjacent interconnecting legs 84, though such is not required. In this unitized cage embodiment, the ring binding mechanisms 80a and 80b are deployed together as an assembly such that the interconnecting legs 84 secure both of the ring binding mechanisms 80a and 80b, or alternatively a pair of rings 80c, as described above.

Figure 22H:
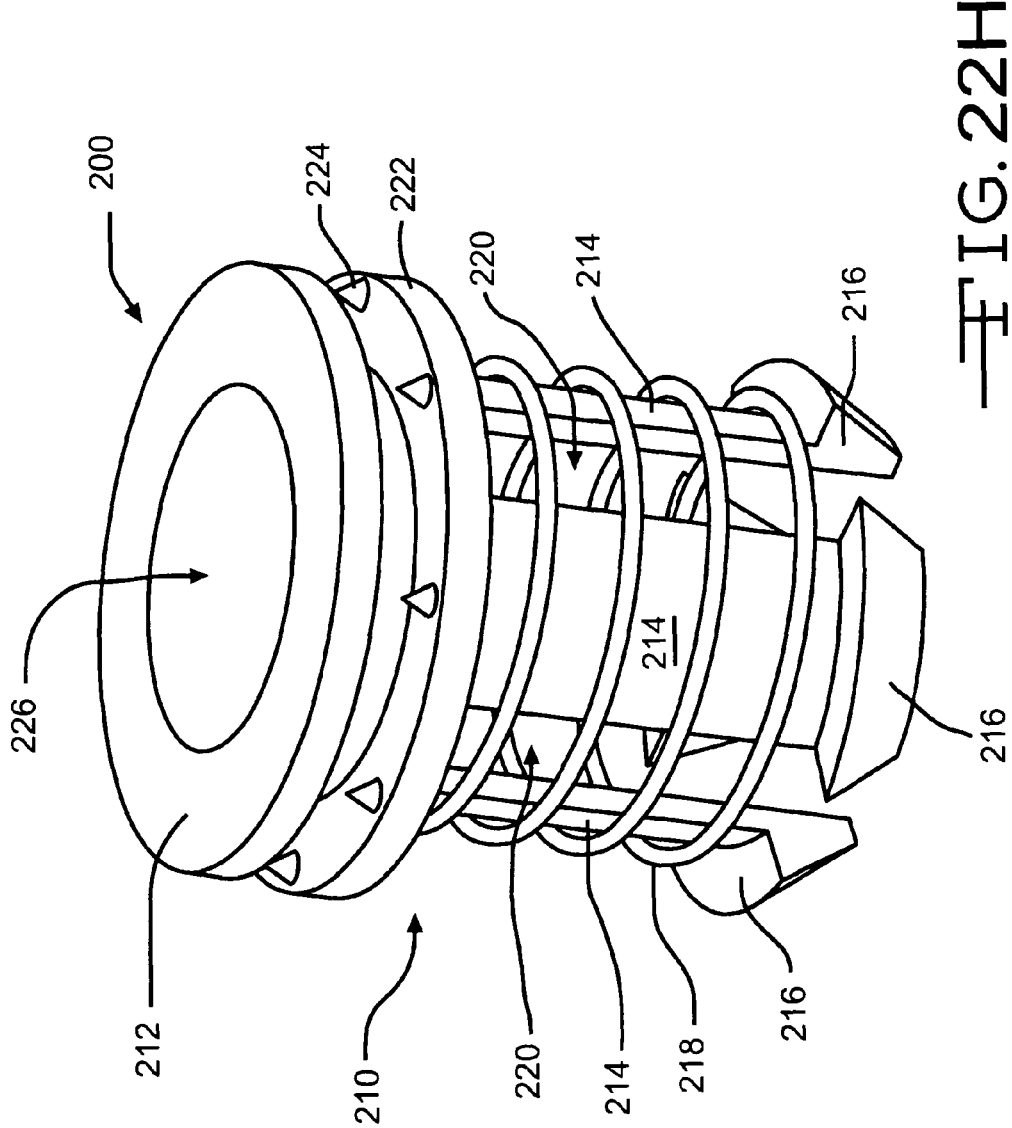
FIG. 22H is an enlarged perspective view of a ring binding mechanism, shown in the clamped position.

Referring now to FIGS. 22G and 22H, there is illustrated another embodiment of a binding mechanism shown generally at 200. The binding mechanism 200 includes a clamping suction port 210 having a ring portion 212 and finned legs 214. The finned legs 214 include a spring clip 216 that retains a resilient member 218, such as for example a coil spring. The resilient member 218 can be any element that provides a reactive force generated by a portion of the element traversing through a distance, thus producing a load/deflection characteristic. Furthermore, the finned legs 214 may be resilient elements that are outwardly biased. The outwardly biased legs 214 may be such that a component of the spring energy is directed upward when moving from an inward to an outward position. Disposed between adjacent finned legs 214 are suction apertures 220 that function in a similar manner to the openings 25 of the tissue collection member 26 as described above.

The resilient member 218, when configured as a separate element such as, for example, a coil spring, is positioned between the spring clips 216 and a clamping ring 222. The clamping ring 222 may further include clamping spikes 224 that project towards the ring portion 212. While not shown, the ring portion 212 may also include clamping spikes that project toward the clamping ring 222. In operation, tissue is drawn in toward the suction apertures 220 by application of a negative pressure, suction, or vacuum from an external vacuum source (not shown). Once drawn in, the finned legs 214 move inward releasing the clamping ring 222. The resilient member 218 directs the claming ring 222 toward the gathered tissue and applies a compressive load thereto. FIG. 22H illustrates the binding mechanism 200 in a clamped configuration. The tissue structures a stoma 54, which may also be sized by a stoma aperture 226.

As illustrated in the embodiment shown in FIGS. 8 and 9, the tissue collection member 26 can be positioned between the barrier disc 44 and the perforated suction tip 24. In one embodiment, the tissue collection member 26 includes a plurality of fins 21 and a plurality of openings 25. The fins 21 may be at least two in number and are spaced apart adjacent to the openings 25. The number, size, stiffness, construction, and material are based, in part, on the intended application and may be more or less than described herein and remain within the scope of the invention. For example in constructing a stoma 54 suitable for gastroplasty surgery, as illustrated in FIGS. 6 and 7, the fins 21 may number between four and six spaced relatively equally apart, with an opening 25 disposed between adjacent fins 21. The fins 21 cooperate with the openings 25 to provide a pleating or bunching of tissue when the vacuum is applied. In the operation this embodiment of the ER apparatus 20, the vacuum source creates a negative pressure which is communicated from the suction tube 32 through the piston 34 via the aperture 33 to the perforated suction tube 46. The suction tube 46 communicates the negative pressure to the tissue collection member 26 via the first perforated section 47a which is generally aligned with the openings 25. The suction tube 46 further communicates the negative pressure to the perforated suction tip 24 via the second perforated section 47b. The perforated suction tip 24 includes a guide wire aperture 27, and a plurality of tip perforations 23 that communicate between the stomach cavity 18 and the perforated suction tube 46. Under the force of the negative pressure, any portion of the contents of the stomach cavity 18, both liquid and gas, may be evacuated through the suction tube 32 by the vacuum, though such evacuation of the stomach cavity is not required. The tissue is also drawn into the openings 25 of the tissue collection member 26 and may further be drawn into the center of the tissue collection member 26 until making contact with a portion of the perforated suction tube 46.

Figure 5:
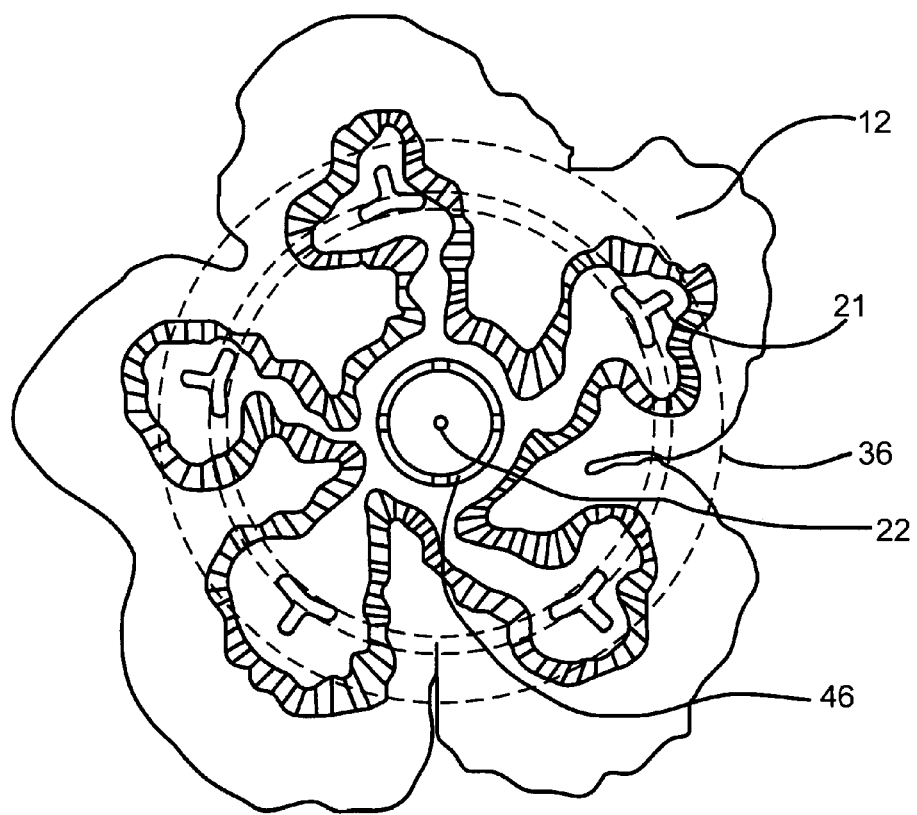
FIG. 5 is a cross sectional view of the constricted section of stomach organ of FIG. 4 taken along section line 5-5.

The fins 21 may be provided with a solid interior surface or may be hollow depending on the radial stiffness required of the tissue collection member 26 to maintain an appropriate standout of tissue, as generally depicted in FIGS. 4 and 5. In certain applications, the fins 21 may be flexible to provide a minimal standout for tissues of thinner wall section, to create a stoma 54 capable of an adaptable or expandable size, or to completely constrict a vessel or lumen, as in tubal ligation procedures. The fins 21 may be drawn inwardly with the tissue as a result of the force of the negative pressure applied to the tissue by the tissue collection member 26. In an alternative embodiment, the fins 21, though depicted as of a solid, smooth surface construction may be segmented, similar to the barbs of a feather or a dart fletching. The feather-like barbs may resemble the teeth of a comb and project substantially radially outward from the tissue collection member 26. The fins 21, so constructed, may allow the coil suture type binding mechanism 36 to pass through the fins 21 without retaining a portion of the tissue collection member 26 along with the tissue.

The fins 21 may be constructed of a medical-grade plastic material similar to the outer tube 30, if so desired. The fins 21, in one embodiment, can be drawn inwardly with the tissue so that the coil suture type binding mechanism 36 could pass over the fins 21 and into the tissue. In an alternative embodiment, the fins 21 may be constructed of a biodegradable material and may additionally be pierced and retained within the stoma. Such a retention of the fins 21 could serve to buttress the coil suture type binding mechanism 36 and function as a pledget for the coil suture type binding mechanism 36 against the stomach wall, if so desired.

FIGS. 24A and 24B illustrate an alternative embodiment of the fins 21. The fins 21 each include a pair of pivots 60, an embodiment of which is shown in FIG. 24C, one end of which is connected to the outer tube 30. Alternatively, the one end of the pivots 60 may be connected to a rotary deployment tube 62a. The rotary deployment tube 62a may be positioned between the suction tube 32 and the outer tube 30 and configured for relative rotation therebetween. The pivots 60 provide an articulable connection between the rotary deployment tube 62a, or outer tube 30, and the fins 21 at a proximal end of the tissue collection member 26. The pivots 60 may also provide an articulable connection between the perforated suction tip 24 and a distal end of the tissue collection member 26. When the ER apparatus 20 is positioned relative to the gastroesophageal junction 16, as illustrated in FIG. 2 or another position as may be clinically indicated, the rotary deployment tube 62a or the outer tube 30 may be rotated to deploy the fins 21 from a closed position, shown in FIG. 24A, to a deployed or open position, shown in FIG. 24B.

In an alternative embodiment, an assembly comprising at least one of the suction tube 32, piston 34, and coil chamber 40 may be rotated to orient the fins 21 into the appropriate position. The fins 21, when in the closed position, may be folded against the outer circumference of the tissue collection member 26 such that each of the fins 21 may lie in a plane that is substantially tangent to the circumference of the tissue collection member 26. When in the deployed position of FIG. 24B, the fins 21 may be fully articulated outwardly to a substantially perpendicular, radially extended orientation relative to the circumference of the tissue collection member 26. The fins 21 may also be partially deployed such that they project in an outward orientation between the closed and open positions. The partial deployment of the fins 21 may provide the ability to vary the resultant stoma size using a single ER apparatus 20 without the need for a plurality of pre-sized suction ports 26. The variable stoma size may further be adjusted during a bariatric procedure in response to newly acquired data or a revised medical opinion.

FIGS. 25A and 25B illustrate an alternative embodiment where the fins 21 include a plurality of fin segments 21a, 21b, and 21c. The fin segments 21a, 21b, and 21c are each connected together in a sequential orientation by a plurality of hinge elements 65 disposed therebetween. The hinge elements 65 may be "living hinges" where a substantially thinned section of the fin material connects each of the adjacent fin segments 21a, 21b, and 21c. Alternatively, the hinge elements 65 may be an articulated joint have two components that move relatively to one another, such as for example a yoke or sleeve and pin, as shown in FIG. 25C, yoke and ball, ball and socket construction, and the like. The fin segments 21a, 21b, and 21c are each oriented in a substantially linear arrangement in the closed or pre-deployed position. The outer tube 30 may be connected to the fin segment 21a by the hinge element 65. Alternatively, an axial deployment tube 62b may be connected to the fin segment 21a by the hinge element 65. The perforated suction tube 24 may also be connected to the fin segment 21c by the hinge element 65. The fin segments 21a, 21b, and 21c may be deployed by pulling the perforated suction tube 24 toward the outer tube 30. Alternatively, the axial deployment tube 65b, or the outer tube 30, may be pushed toward the perforated suction tube 24 in order to articulate the hinge elements 65 and project the fins 21 in an outward direction, as shown in FIG. 25B. Alternatively, the axial deployment tube 65b may be connected to the perforated suction tube 24 such that deployment of the fins 21 may be effected by pulling the axial deployment tube 65b relative to the outer tube 30.

FIGS. 26A and 26B illustrate another alternative embodiment of a fin deployment structure and method where the fins 21 include fin segments 21a, 21b, and 21c that are each sequentially attached by hinged elements 67 similarly oriented as in FIGS. 25A and 25B. The fin segments 21a-21c are hinged with respect to each other and to their respective ER apparatus mounting points. The hinge elements 67 of the alternative embodiment are biased or pre-stressed such that their natural or unrestrained state is in an outwardly projecting orientation, as best shown in FIG. 26B. The outwardly biased state may be formed into the hinge elements 67 and the fin segments 21a-21c or the components may be made from a shape memory material having the projected shape as the unrestrained structure. An embodiment of an outwardly biased "living hinge" 67 is shown in FIG. 26C.

The outer tube 30 may cover the fin segments 21a-21c, or alternatively, an outer deployment tube 62c may be disposed over the outer tube 30 and the fin segments 21a-21c to allow the ER apparatus 20 to be inserted, located, and inflated or expanded. In another embodiment of the invention, the fin segments 21a-21c may be covered in a hood structure 90a, as shown in FIG. 26A prior to deployment. Once the ER apparatus 20 is properly deployed and inflated or expanded, the suction tube 32 and perforated suction tube 42 may be pushed further into the stomach cavity 18 to expose and deploy the fin segments 21a-21c. Alternatively, the outer deployment tube 62c may be retracted to expose and deploy the fin segments 21a-21c.

Referring again to FIG. 8, the assembled ER apparatus 20 description preferably begins at the guide wire aperture 27 of the perforated suction tip 24 which is the end proximal to the introduction point at the patient, typically the oral cavity. The second perforated section 47B of the perforated suction tube 46 may be coaxially disposed within the perforated suction tip 24. A linear space may be provided between the guide wire aperture 49 of the perforated suction tube 46 and the interior end of the perforated suction tip 24 to allow relative axial movement therebetween. The relative axial movement occurs during the binding mechanism deployment in the embodiment where the perforated suction tube 46 is made as an integral part of the suction tube 32 and/or the piston 34. The tissue collection member 26 end proximal to the patient introduction point is fixed to the distal end of the perforated suction tip 24. The tissue collection member 26 may be generally aligned with and coaxial to the first perforated section 47a. The barrier disc 44 is fixed between the distal end of the tissue collection member 26 and the proximal end of the coil chamber 40 and aligned such that the center aperture 45 is generally coaxially oriented with the tissue collection member's 26 axial centerline. The non-perforated portion 48 is positioned through the center aperture 45 and connected to the aperture 33 of piston 34.

The piston 34 is seated at or near the connection of the outer tube 30 and the coil chamber 40. The deployment nib 35 is disposed within the distal end of the helical groove 42 in the coil chamber 40. The blunt end of the coil suture type binding mechanism 36 is disposed within the helical groove 42 proximal to and may be in contact with the deployment nib 35. The piston 34 is fixed to the suction tube 32 which is coaxially oriented to the outer tube 30 and the coil chamber 40. The suction tube 32 is coaxially oriented within the outer tube 30. The inflation tube 29 is parallel with or integrated into the outer tube 30. The suction tube 32 preferably extends beyond the outer tube 30 and terminates in a suitable coil actuating apparatus (not shown), examples of which are disclosed in U.S. Pat. No. 5,824,008 to Bolduc et al. which is expressly incorporated herein by reference in its entirety. Other types of coil sutures may be used. It is to be understood, that in certain embodiments, a suitable coil actuating apparatus may alternatively include a simple hand wheel structure to rotate the suction tube 32 relative to the outer tube 30 in an appropriate direction. The suction tube 32 may extend beyond the coil actuating apparatus or accessed by any other device in order to operatively connect to an external vacuum source.

The ring binding mechanisms 80a, 80b, and 80c may be deployed in a similar manner to the coil suture type binding mechanism 36, if so desired. Alternatively, the ring binding mechanisms 80a, 80b, and 80c may be axially deployed by way of an axial deployment tube or structure similar to deployment tube 62b shown in FIG. 25A. Furthermore, the ring binding mechanisms 80a, 80b, and 80c may substituted for the coil suture type binding mechanism 36 to effect to method of the invention, as described below. Additionally, the method of the invention described below is intended to accommodate the variations to the deployment of the stoma creating devices, as described above, by substituting the appropriate procedural measures.

The method of creating a stomatic restriction, for example as part of an endolumenal restriction procedure, begins with a medical evaluation, typically conducted with an upper endoscopy. Based on the medical judgment resulting from the endoscopic evaluation, the guide wire 22 is inserted into the stomach cavity 18 through the endoscope (not shown). The endoscope may then be removed and the ER apparatus 20 may then be introduced over the exposed end of the guide wire protruding from the patient's mouth. The ER apparatus 20 may be preferably provided as a complete device kit comprising a fully assembled ER apparatus including various suction port configurations and various coil sizes, along with other fittings and adapters. Alternatively, the ER apparatus may have portions that are preassembled and presented for use allowing one of ordinary skill in the art to select the needed components of appropriate size, material, and construction for the application. The kit portions may be selectable and configurable in such a manner as to require minimal assembly.

The ER apparatus 20 may be threaded onto the guide wire 22 as a completed assembly. First, the perforated suction tip 24 is threaded onto the guide wire 22 through the guide wire aperture 27. The guide wire 22 is next manipulated into the guide wire aperture 49 of the perforated suction tube 46. The guide wire 22 passes through the perforated suction tube 46 and the aperture 33 of the piston 34 to the suction tube 32. Once the guide wire 22 has been initially threaded into the ER apparatus 20, preferably to the level of the end of the suction tube 32 that is proximal to the patient, the ERG apparatus 20 is ready for deployment into the patient. The ER apparatus 20 is urged into the esophagus 14 and finally into the stomach cavity 18. The depth of initial insertion of the ER apparatus 20 is determined by medical judgment based on prior examination results and verified by depth indicia on the outer tube 30. The final location verification may occur after the balloon type lumen sizing structure 28 is inflated and drawn toward the gastro-esophageal junction 16 or other suitable location. The final location verification may be a tactile resistance to withdrawal of the ER apparatus 20 and/or a visual, numerical check of depth indicia on the outer tube 30.

The operation of the ERG apparatus 20 begins with the apparatus located in the appropriate position within the stomach cavity 18. The balloon 20 is inflated with fluid, i.e. air, saline, water, or other suitable mediums, or expanded mechanically as described above. The ER apparatus 20 is partially withdrawn to locate the balloon type lumen sizing structure 28 at the gastro esophageal junction 16, or other suitable location indicated by medical judgment. When a resistance to withdrawal of the inflated ER apparatus 20 is felt, or numerically verified by some indicia, the ERG apparatus 20 is in position, such as, for example, located approximately as depicted in FIG. 2. The suction tube 32 is attached to the external vacuum source. The vacuum source is energized and operated for a predetermined time, for example approximately 30 seconds or some other time frame based on medical judgment. Once the vacuum source has evacuated the desired amount of the contents of the stomach cavity 18, if any, the resulting stomach 12 may appear similar to the depiction of FIG. 3. The stomach cavity 18, or at least a portion of the cavity, may contact the perforated suction tip 24. The area targeted to create the stoma 54 may be gathered around the tissue collection member 26, as described above. The new gastric pouch 52 is formed around the inflated balloon type lumen sizing structure 28, as illustrated in FIG. 3. The gastric pouch 52 is also shown in FIGS. 6 and 7 with alternate embodiments of the orientation of the stoma 54 to the coil suture type binding mechanism 36.

FIG. 4 shows an enlarged view of the deployment of the coil suture type binding mechanism 36 from the coil chamber 40. The operator engages the coil deployment apparatus, of a type suitable for the intended purpose as described above, and initiates deployment of the coil suture type binding mechanism 36. The coil suture type binding mechanism 36 is pushed from the coil chamber 40 by the deployment nib 35, which follows the engaged path of the helical groove 42. The exit point of the helical groove 42 is aligned with the deployment aperture 43 (see FIG. 9) of the barrier disc 44 and may be oriented between two adjacent fins 21. The piercing end 75*a* or 75*b* of the coil suture type binding mechanism 36 exits through the deployment aperture 43 and expands to its free-state diameter. The coil suture type binding mechanism 36 then encircles the tissue collection member 26 and fins 21. During deployment, the coil suture type binding mechanism 36 pierces the tissue gathered against the tissue collection member 26 and fins 21, preferably as illustrated in FIGS. 4 and 5. Deployment of the coil suture binding mechanism 36 ceases when the coil suture type binding mechanism 36 is fully deployed from the coil chamber 40 and into the target tissue. Deployment is further verified when the piston 34 cannot be further advanced and rests against, for example, the barrier disc 44.

Once the coil suture type binding mechanism 36 is fully deployed and verified as stated above, the vacuum source is de-energized and the balloon type lumen sizing structure 28 is deflated or mechanically contracted. The ER apparatus 20 and the guide wire 22 are removed from the patient. If desired, a repeated endoscopy may be performed to verify the proper condition of the gastric pouch 52 and the newly formed stoma 54, which may be similar to that illustrated in FIGS. 6 and 7. The coil suture type binding mechanism 36 may encircle the exterior of the tissue, as shown in FIG. 6 or may be completely or partially within the tissue, as illustrated in FIGS. 5 and 7.

FIG. 4 depicts the tissue gathered onto the tissue collection member 26 and within the openings 25 of the tissue collection member 26. FIG. 5 illustrates the position of the perforated suction tube 46 within the gathered tissue. The perforated suction tube 46 cooperates with the tissue collection member 26 to accurately size the stoma 54. By providing a positive stopping point for the tissue, the perforated suction tube 46 helps create a repeatable opening size within the stoma 54. The tissue collection member 26 pleats the tissue to further help prevent the opening within the stoma 54 from changing size or collapsing.

At a later time it may be necessary or desirable to remove the coil suture type binding mechanism 36 and the stoma 54. In order to remove the coil suture type binding mechanism 36 and return the stomach to a substantially pre-operative state, an endoscopic grasping device (not shown) may be used. The grasping device engages an end of the coil suture type binding mechanism 36. The coil suture type binding mechanism 36 is "unscrewed" in a direction opposite from the deployment rotation. The coil suture type binding mechanism 36 is then extracted from the stomach cavity 18 and completely removed.

In an alternative embodiment of the removal method, the ring binding mechanisms 80*a*, 80*b*, and 80*c* include the cleavage points 83. A mechanically expandable or fluidly inflatable instrument, or any suitable similar structure, which may be an individual instrument, part of another instrument, or part of the ER apparatus 20, may be positioned within the center aperture 89 of the ring binding mechanisms 80*a*, 80*b*, and 80*c*. For example, in one embodiment, the balloon type lumen sizing structure 28 can be re-inserted into the patient and inflated.

The expandable or inflatable instrument is then inflated or expanded until the cleavage points 83 fracture. The expandable or inflatable instrument is preferably of a sufficient strength to apply a load to actuate the cleavage points 83 in a fracture mode. The expandable or inflatable instrument, and may be constructed differently depending on the construction and residual strength of the ring binding mechanisms 80*a*, 80*b*, and 80*c*. The fractured, separate pieces of the ring binding mechanisms 80*a*, 80*b*, and 80*c* separate from the gathered tissue, either by using instruments to remove the pieces or through the expansion of the stoma 54 during the procedure or subsequent food intake. Once separated from the tissue, the fragments of the ring binding mechanisms 80 may be mechanically extracted or may be passed through the digestive tract by natural processes and excreted.

In another embodiment, the ring binding mechanisms 80*a*, 80*b*, and 80*c* and the interconnecting legs 84 may be disconnected in a reverse manner to the installation method described above. For example. the rings 80*a* and 80*b* and interconnecting legs 84 having buttons 86 may be grasped from inside the stoma 54 and rotated relatively such that the button 86 may be withdrawn from hole 85*b*. Alternatively, the buttons 86 may be provided with cleavage points to allow a sufficient axial strain to uncouple the rings 80*a* and 80*b*.

In another aspect, there is provided herein an endolumenal restriction (ER) removal apparatus 100, as schematically illustrated in FIGS. 28-36. In certain embodiments, the ER removal apparatus 100 can be used in a method of restriction removal, in accordance with various embodiments of the invention, as described herein. Only those parts or components necessary for an understanding of the construction and operation of the apparatus will be described. Where possible, like reference numbers are used to designate features and elements that are common or to indicate corresponding parts.

Referring now to FIG. 28, the ER removal apparatus 100, shown in an insertion configuration, includes an outer tube 130, an inner tube 132, an extraction hood 128, an extraction cylinder 150, and a tapered tip 124. The ER removal apparatus 100 may be made from a flexible material, such as plastics suitable for surgical applications. The outer tube 130 may be provided with calibrated markings (not shown) or other indicia suitable to determine the length of the device that has been inserted into the patient. The calibrated markings allow for an accurate positioning of the device within the stomach cavity 18 relative to a datum point on the patient, such as the incisors. The ER removal apparatus further includes a guide wire 122, which can be inserted during an endoscopic examination procedure.

In one embodiment, the ER removal apparatus 100 further includes an extraction hood 128, which may be fixed to the outer tube 130. In the insertion configuration of FIG. 28, the extraction hood 128 may be contained against the outer tube 130 by a release line 135, or other such retaining mechanism, such as for example an outermost restraining tube, a coiled sleeve, a tear-away pull-tab release, and the like, if so desired though such is not required.

As shown in FIG. 28, the extraction cylinder 150 is attached to the inner tube 132 for rotation relative to the stationary outer tube 130. The extraction cylinder 150, shown in FIGS. 31 and 32, includes a locating channel 152 that terminates in an inwardly-projecting, radial end groove 155. The radial end groove 155 is shown in FIG. 28 oriented toward the outer tube 130, though such an orientation is not required. The locating channel 152 may have an inwardly tapering surface directed toward the end groove 155. The end groove 155 structures a slight interference fit with the mating coil piercing end 75*b* or the ring removal barbs 82. The slight interference fit may be against the outer or inner surface of the coil piercing end 75*b* or the ring removal barb 82, if so desired, to aid in securely locating the coil suture type binding mechanism 36 or ring binding mechanisms 80*a*-80*c* to the extraction cylinder 150.

FIG. 29 shows the ER removal apparatus in the removal configuration with the extraction hood 128 free to expand radially. If so included, the release line 135, or other restraining device is removed to allow the extraction hood 128 to open in order to cover the removed coil suture type binding mechanism 36 or ring binding mechanisms 80*a* and 80*b*. FIG.

29 further illustrates an alternate embodiment of the tapered tip 124 that includes a tip access notch 126 to ease location of the coil piercing end 75b into the extraction cylinder 150, though such is not required. In the alternate embodiment of FIG. 29, the radial end groove 155 is oriented toward the tapered tip 124. The tapered tip 124 further includes a guide wire aperture 127 formed in the end to allow passage of the ER removal apparatus 100 over the guide wire 122. FIG. 30 illustrates another embodiment of a ER removal apparatus 100 in an extraction configuration where the extraction hood 128 is positioned over the removed coil suture type binding mechanism 36 or ring binding mechanisms 80a-80c.

Figure 33:
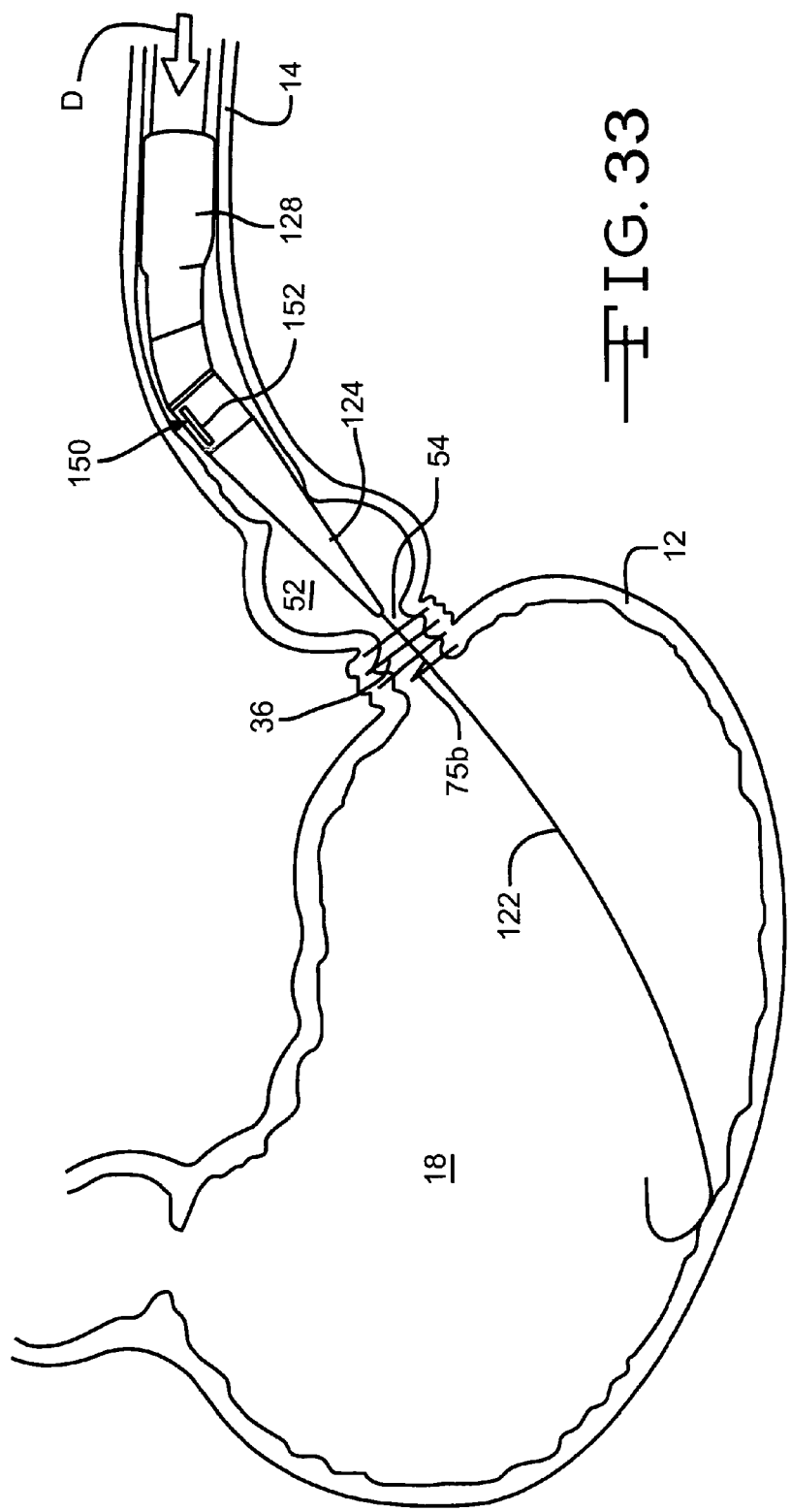
FIG. 33 is a front elevational view, partially in cross section, of an endolumenal restriction removal apparatus inserted into a human stomach.

FIGS. 33-36 illustrate one removal method where, after the guide wire is inserted into the stomach cavity 18 as described above, the ER removal apparatus 100 is threaded onto the guide wire 122, with the tapered tip 124 introduced first. The ER removal apparatus 100 is gently urged down the esophagus 14, as indicated by directional arrow D. The ER removal apparatus 100 is preferably in the insertion configuration shown in FIG. 28, though such is not required. The ER removal apparatus 100, as shown in FIG. 33, reaches the gastric pouch 52 where the tapered tip 124 pushes through the stoma 54. The tapered tip 124 is sized such that a first portion of the end is small enough to pass through the coil suture type binding mechanism 36 or ring binding mechanism 80 and the stoma 54. As the tapered tip 124 passes through the stoma 54, the increasing size of the tip diameter begins to press against the inner wall of the stoma 54 to slightly expand the coil suture type binding mechanism 36 or the ring binding mechanisms 80a and 80b. The slight expansion of the stoma 54 facilitates the location of the coil piercing end 75b or the ring removal barbs 82 in the inwardly-projecting, radial end groove 155 and the locating channel 152. As the tapered tip 124 slides against the coil piercing end 75b or the ring removal barb 82, the locating channel 152 contacts the end 75b or barb 82 to capture and guide the end 75b or barb 82 toward the radial end groove 155. The coil piercing end 75b or removal barbs 82 snap inwardly into position within the radial end groove 155 at the end of the locating channel 152.

Figure 34:
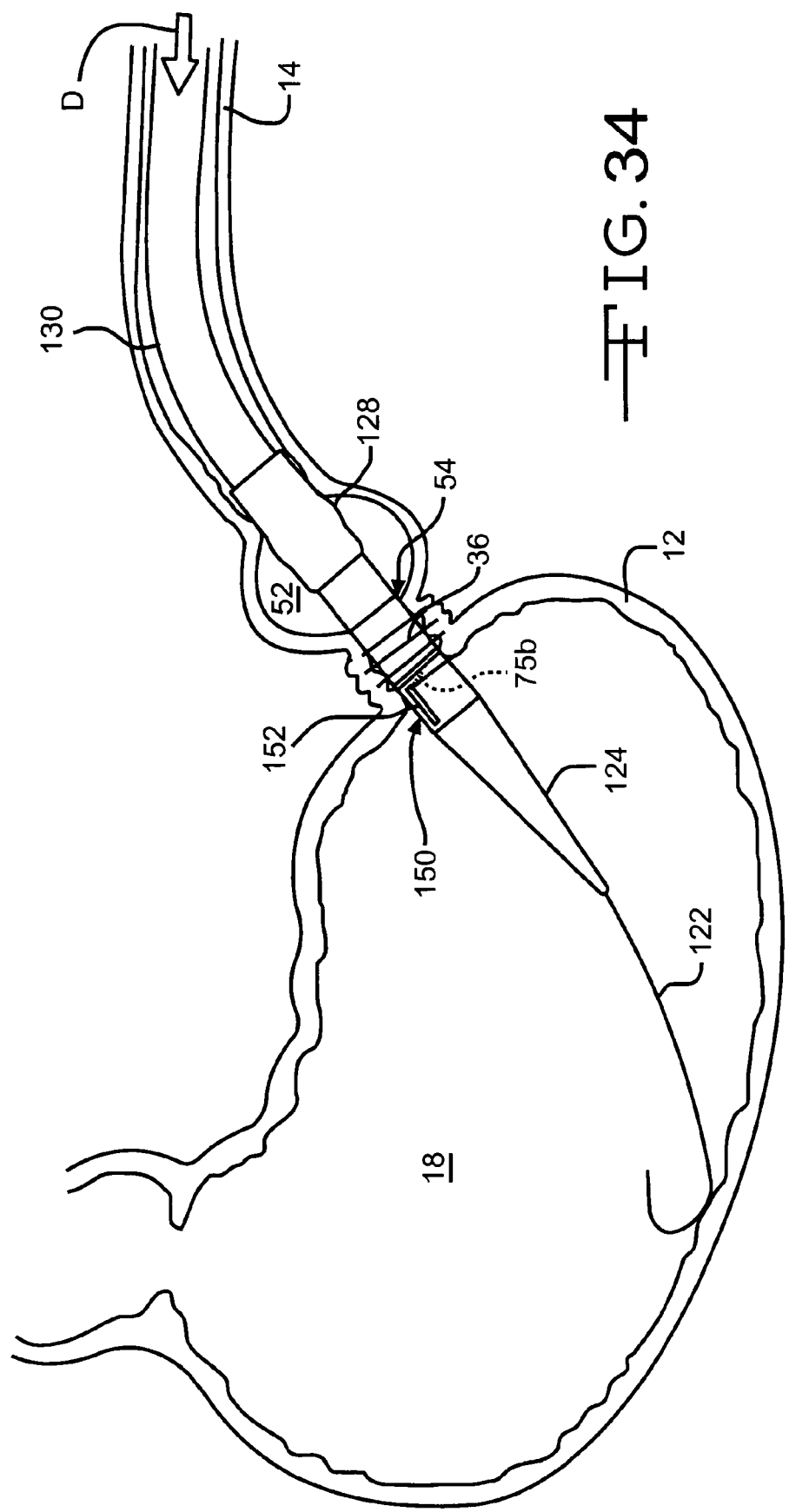
FIG. 34 is a front elevational view, partially in cross section, of the endolumenal restriction removal apparatus of FIG. 33 engaging the coil or ring binding mechanism.

FIG. 34 shows the piercing end 75b engaging the locating channel 152 and the radial end groove 155. The piercing end 75b snaps within the radial end groove 155 with a sufficient interference fit to stably support and rotate with the extraction cylinder 150. Once engaged, the inner tube 132 and the extraction cylinder 150 are rotated in the same direction as the coil suture type binding mechanism 36 or ring binding mechanisms 80a and 80b were inserted to create the stoma 54. The coil suture type binding mechanism 36 or ring binding mechanism 80a-80c can then be unscrewed out of engagement with the gathered tissue. The ER removal apparatus 100 then advances further into the stomach cavity 18, as shown in FIG. 35.

Figure 35:
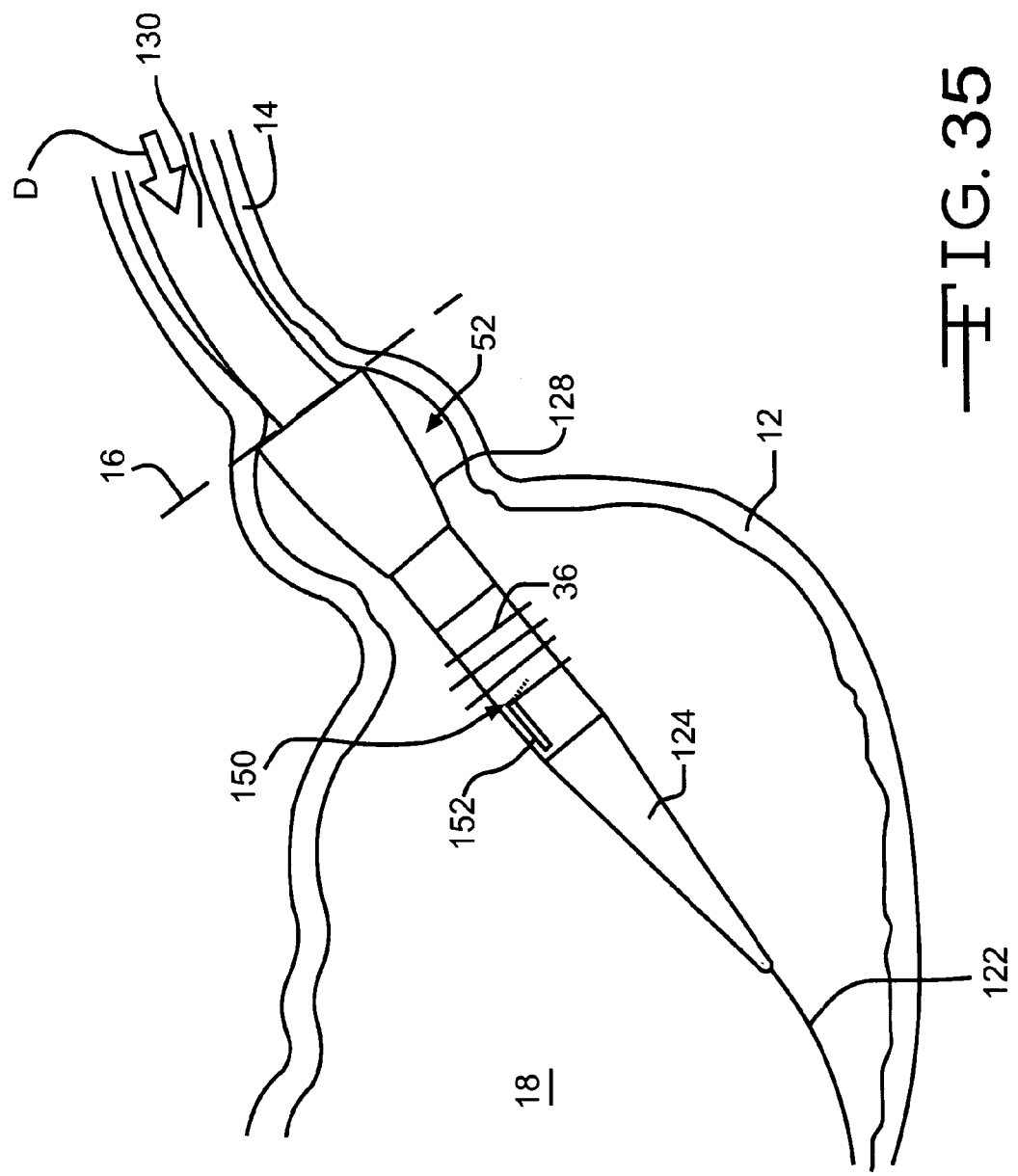
FIG. 35 is a front elevational view, partially in cross section, of the endolumenal restriction removal apparatus of FIG. 34 removing the coil or ring binding mechanism.
Figure 36:
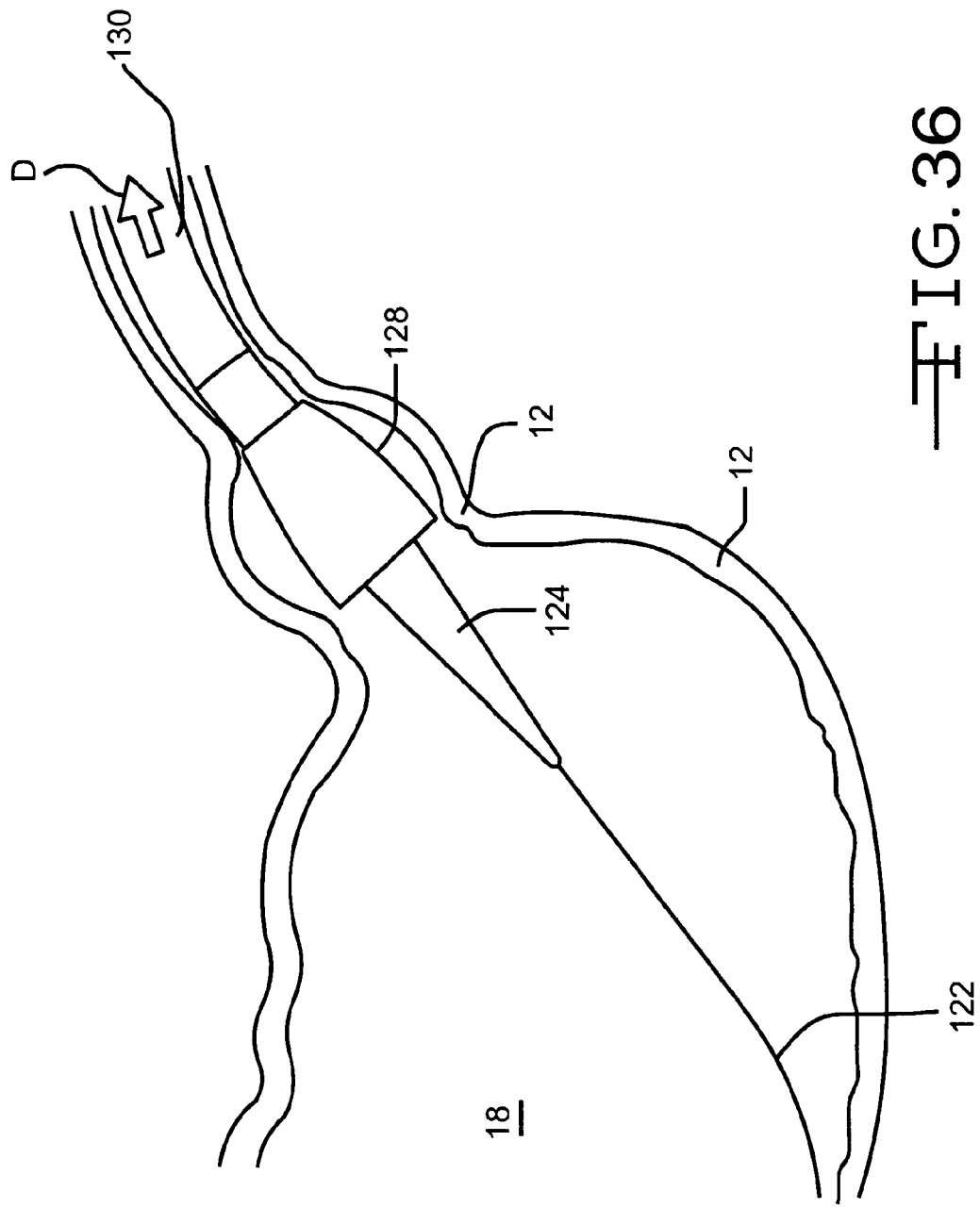
FIG. 36 is a front elevational view, partially in cross section, of the endolumenal restriction removal apparatus of FIG. 35 during an extraction of the coil or ring binding mechanism.

FIG. 35 illustrates the coil suture type binding mechanism 36 wound around the extraction cylinder 150 and positioned within the stomach cavity 18. The ER removal apparatus 100 advances a sufficient distance so that the extraction hood 128 is beyond the gastro-esophageal junction 16. If the release line 135, or other restraining device has not been removed, it may be removed to allow the extraction hood 128 to expand radially outward. Once expanded, the open end of the extraction hood 128, and the ER removal apparatus 100, may be retracted a sufficient distance to locate against the gastro-esophageal junction 16 or other suitable location. Continued extraction of the ER removal apparatus 100 causes the extraction hood 128 to roll over and envelop the coil suture type binding mechanism 36. Once covered, the ER removal apparatus 100 may be extracted through the esophagus 14 without the coil suture binding mechanism 36 abrading or otherwise damaging other patient tissues, as shown in FIG. 36.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

What is claimed is:

1. An endolumenal restriction apparatus for non-surgically creating a restriction in a tubular organ of a patient, comprising:
   a tissue collection member configured for at least partially gathering a portion of tissue of the tubular organ;
   a deployment mechanism configured for inserting a binding mechanism circumferentially around the tissue collection member and into the gathered tissue to form the restriction in the tubular organ; and
   an elongated and flexible delivery mechanism configured for advancing the tissue collection member and the deployment mechanism within the tubular organ.

2. The apparatus of claim 1, wherein the tissue collection member is configured to allow at least a portion of the gathered tissue to define a stoma through which matter may pass.

3. The apparatus of claim 1, wherein at least a portion of the endolumenal restriction apparatus is configured to be endoscopically inserted into the patient.

4. The apparatus of claim 1, wherein the tissue collection member includes a plurality of fins that define an interior space into which tissue of the organ enters.

5. The apparatus of claim 4, wherein the tissue collection member comprises outwardly extending fins disposed about the interior space.

6. The apparatus of claim 1, wherein the endolumenal restriction apparatus further includes at least a first perforated section configured to provide a first negative pressure against the organ.

7. The apparatus of claim 6, wherein the endolumenal restriction apparatus further includes a second perforated section configured to provide a second negative pressure against the organ.

8. The apparatus of claim 1, wherein the deployment mechanism comprises a chamber for receiving the binding mechanism and a device disposed between the tissue collection member and the chamber for advancing the binding mechanism into the gathered tissue.

9. The apparatus of claim 8, wherein the chamber includes a helical groove having at least one turn formed into an inner surface of the chamber and configured to locate or guide the binding mechanism into the gathered tissue.

10. The apparatus of claim 8, wherein the binding mechanism comprises a coil suture having at least one turn.

11. The apparatus of claim 1, wherein the tissue collection member is configured to allow at least a portion of the gathered tissue to define a stoma through which matter may pass.

12. The apparatus of claim 1, further comprising a lumen sizing structure configured to define a lumen from tissue of the patient.

13. The apparatus of claim 12, wherein the lumen sizing structure comprises a balloon.

14. The apparatus of claim 12, wherein the lumen sizing structure is located proximal to the tissue collection member.

15. The apparatus of claim 1, wherein the tissue collection member comprises a peripheral frame having an axial center line, the peripheral frame defining at least two openings spaced about the axial center line, wherein the tissue collection member is configured to allow a portion of tissue of the tubular organ to be drawn into the openings and towards the axial center line.

16. The apparatus of claim 1, wherein the tissue collection member defines an interior space and is configured for at least partially gathering a portion of tissue of the tubular organ circumferentially around the tissue collection member and for drawing a portion of tissue of the tubular organ into the space and wherein the deployment mechanism is configured for inserting the binding mechanism circumferentially around the tissue collection member and into the circumferentially gathered tissue to form the restriction in the tubular organ.

17. An endolumenal restriction apparatus for creating a stoma in a tubular organ of a patient having an organ cavity and an organ cavity wall, the endolumenal restriction apparatus comprising:
   a lumen sizing structure configured to define a size of a lumen formed from a first portion of the organ cavity wall;
   a tissue collection member configured to be positioned at least adjacent to the sized lumen, the tissue collection member defining an interior space, the tissue collection member being configured to outwardly support at least a second portion of the organ cavity wall and to allow at least a third portion of the organ cavity wall to enter the interior space; the third portion of the organ cavity wall comprising gathered tissue, the gathered tissue defining a stoma through which matter may pass; and
   a deployment mechanism configured: i) to insert a binding mechanism circumferentially around the tissue collection member and into the gathered tissue while maintaining the stoma, and ii) to position the binding mechanism in engagement with the gathered tissue to bind the gathered tissue, thereby maintaining the defined size of the lumen.

18. The apparatus of claim 17, wherein the organ comprises one of: a stomach, a fallopian tube, a vagina, a urethra, a ureter, an esophagus, an intestinal tract, a bronchial tube, an ear canal, and a nasal passageway.

19. An endolumenal restriction apparatus kit, the kit comprising the endolumenal restriction apparatus of claim 17 and at least one binding mechanism.

20. A method for creating a restriction in a tubular organ having an organ cavity and cavity wall in a patient, the method comprising:
   providing an endolumenal restriction apparatus, wherein the endolumenal restriction apparatus comprises a tissue collection member a deployment mechanism;
   advancing the tissue collection member and deployment mechanism into the organ cavity using an elongated and flexible delivery mechanism;
   gathering tissue of the tubular organ around the tissue collection member;
   deploying a binding mechanism with the deployment mechanism, wherein the binding mechanism is deployed circumferentially around the tissue collection member and into the gathered tissue to form the restriction in the tubular organ.

21. The method of claim 20, wherein the tissue collection member and deployment mechanism are inserted into the patient through a natural body opening of the patient.

22. The method of claim 20, further comprising advancing a lumen sizing structure into the tubular organ and sizing a lumen in the tubular organ.

23. The method of claim 20, wherein the sized lumen is located proximal to the tissue collection member.

* * * * *

UNITED STATES PATENT AND TRADEMARK OFFICE
CERTIFICATE OF CORRECTION

PATENT NO. : 8,591,533 B2  
APPLICATION NO. : 12/526157  
DATED : November 26, 2013  
INVENTOR(S) : Needleman et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 718 days.

Signed and Sealed this
Twenty-first Day of April, 2015

Michelle K. Lee
*Director of the United States Patent and Trademark Office*